United States Patent [19]

Oleksyszyn et al.

[11] Patent Number: 5,677,282
[45] Date of Patent: Oct. 14, 1997

[54] AMINO ACID AMIDES OF 1,3,4-THIADIAZOLES AS MATRIX METALLOPROTEINASE

[75] Inventors: Jozef Oleksyszyn, Arlington; Alan R. Jacobson, Somerville, both of Mass.

[73] Assignee: Proscript, Inc., Cambridge, Mass.

[21] Appl. No.: 473,143

[22] Filed: Jun. 7, 1995

[51] Int. Cl.⁶ .................. C07K 5/08; C07K 5/06; A61K 31/41
[52] U.S. Cl. .................. 514/118; 514/19; 514/363; 514/364; 530/330; 530/331; 548/139; 548/144
[58] Field of Search .................. 548/139, 144; 530/330, 331; 514/18, 19, 363, 364

[56] References Cited

FOREIGN PATENT DOCUMENTS

3407505A1   9/1985   Germany .
61-161281   7/1986   Japan .

OTHER PUBLICATIONS

Cho, N. S. and Kim, G. N., "Synthesis of 5–Aroylamino–3H–1,3,4–Thiadiazole–2–Thiones and Their Tautomerism," *J. Heterocyclic Chem.*, 30:397 (1993).

Suiko, M., et al., "Relationship Between the Structures and Cytotoxic Activities of 1,3,4–Thiadiazolo[3,2–α]pyrimidines," *Agric. Biol. Chem.*, 46(11):2691–2695 (1982).

*Primary Examiner*—Robert Gerstl
*Attorney, Agent, or Firm*—Sterne, Kessler, Goldstein & Fox, P.L.L.C.

[57] ABSTRACT

Amino acid amides of 5-amino-1,3,4-thiadiazole-2-thione are disclosed. These compounds inhibit matrix metalloproteinase enzymes and cartilage degradation. Methods of treating diseases caused by over-activity of matrix metalloproteinases, such as osteoarthritis and rheumatoid arthritis, are also disclosed.

17 Claims, No Drawings

AMINO ACID AMIDES OF 1,3,4-THIADIAZOLES AS MATRIX METALLOPROTEINASE

BACKGROUND

Matrix metalloproteinases are a class of zinc-dependent, proteolytic enzymes. These enzymes play a role in a number of disease processes.

Increased levels of collagenase and stromelysin have been observed in synovium and cartilage in several arthritic disease (Dean, et al., *J. Clin. Invest.*, 84:678 (1989) and the levels correlate with the severity and advancement of the disease (Blanckaert, et al., *Clin. Chim. Acta*, 185:73 and Valakovits, et al., *Arthr. Rheum.*, 35:35 (1992)). They have also been linked to cartilage matrix degradation (Brown, et al., *J. Med. Chem.*, 37:674 (1994) and Gordon, et al. *Clin. Exp. Rheumatol.* 11 (*Supplement* 8):S91 (1993)). Matrix metalloproteinases also contribute to cartilage degradation by cleaving $\alpha_1$-antiproteinase inhibitor-1, thereby removing its ability to inactivate human neutrophil elastase. Furthermore, it has been shown in vivo that inhibitors of matrix metalloproteinases are able to inhibit angiogenesis (Garlardy, et al., *Cancer Research*, 54:4715 (1994)), i.e. the formation of new blood vessels. Although angiogenesis occurs in normal processes, such as ovulation, placental development and wound healing, it is also involved in pathological processes such as arthritis and inflammation (D'Armore, et al., *Ann. Rev. Physiol.*, 49:453 (1987)).

Many members of metalloproteinases family were originally described in malignant cell lines and appear to play a role in tumor metastasis (Liotta and Rao, *Lab Invest.*, 49:636-649 (1983)). For example, certain small molecular weight inhibitors of metalloproteinases inhibit the growth of human tumor cells in nude mice (Naito et. al., *Int. J. Cancer*, 58:730-735 (1994)). In addition, angiogenesis is also involved in tumor malignancy (D'Armore, et al.).

Matrix metalloproteinases play critical roles in other pathological processes such as periodontal disease (Birkedal-Hansen, et al., *Crit. Rev. Oral Biol. Med.*, 4:197–250, (1993)), various ulcerated conditions (Brown, et al., *Arch. Opthal.*, 81:370–373 (1969)), and epidermolysis bullosa, (Johnson, et al., *Enzyme Inhibition*, 2:1–22 (1987)).

Many of the pathological processes associated with the diseases could be slowed, arrested or even reversed if the activity of the matrix metalloproteinases responsible for the pathological processes could be inhibited. Although there are known inhibitors of matrix metalloproteinases, e.g. peptidyl hydroxamates, they exhibit poor bioavailablity and are therefore unable to significantly modify the progression of osteoarthritis and other diseases. Consequently, there is a need for new inhibitors of matrix metalloproteinases which can be used as therapeutics.

SUMMARY OF THE INVENTION

This invention is based on the discovery that amino acid amides of 5-amino-1,3,4-thiadiazole-2-thiol are potent and selective inhibitors of matrix metalloproteinases. It has also been found that these compounds can prevent interleukin-1 induced cartilage degradation by matrix metalloproteinases.

One embodiment the present invention is a compound represented by Structural Formula I:

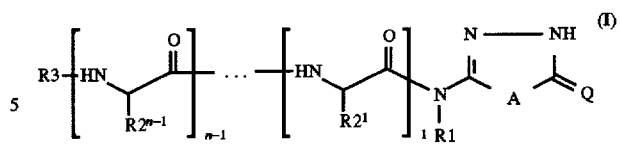

wherein:

Q and A are each independently selected from the group consisting of sulfur and oxygen and one of Q and A is sulfur;

n is a positive integer which results in a matrix metalloproteinase inhibitor;

R1 is selected from the group consisting of —H, lower alkyl and acyl;

each R2 is independently selected from the group consisting of C1–C10 straight or branched alkyl, C1–C10 straight or branched substituted alkyl, C3–C8 cyclic alkyl, substituted C3–C8 cyclic alkyl, C1–C10 straight or branched alkenyl, C1–C10 straight or branched substituted alkenyl, C1–C10 straight or branched alkynyl, C1–C10 straight or branched substituted alkynyl, aryl, substituted aryl, heteroaryl, substituted heteroaryl;

R3 is an amine derivatizing group; or a physiologically active salt thereof.

Another embodiment of the present invention is a method of inhibiting a matrix metalloproteinase. The method comprises contacting the matrix metalloproteinase with a compound having the structure of Formula I.

Yet another embodiment of the present invention is a method of treating a disease in an individual or animal which can be ameliorated by inhibiting at least one matrix metalloproteinase. The method comprising administering to the individual or animal a therapeutically effective amount of a compound having the structure of Formula I.

Amino acid amides of 5-amino-1,3,4-thiadiazole-2-thiones are useful for treating individuals and animals with diseases resulting from over activity of matrix metalloproteinases, such as osteoarthritis, rheumatoid arthritis, cancer and the inflammation associated with many of these diseases. The thiadiazoles of the present invention have other in vivo uses, such as aiding in identifying the location of matrix metalloproteinases in an individual or animal. These thiadiazole compounds are also useful in vitro for preventing the degradation of tissue and proteins present in biological samples containing matrix metalloproteinases, as an aid in identifying new drug targets for the treatment of these diseases and in isolating matrix metalloproteinases.

DETAILED DESCRIPTION OF THE INVENTION

The present invention relates to novel inhibitors of matrix metalloproteinases. Known inhibitors of matrix metalloproteinases comprise an oligopeptide bound to a functional group such as a hydroxamic acid or thiol which can chelate the zinc atom in the active site of the matrix metalloproteinase. It has now been found that aminoacid amides of heterocyclic compounds which are capable of chelating zinc can also inhibit matrix metalloproteinases. The matrix metalloproteinase inhibitors of the present invention include amino acid amides of 5-amino-1,3,4-thiadiazoleo-2-thiol represented by Structural Formula II:

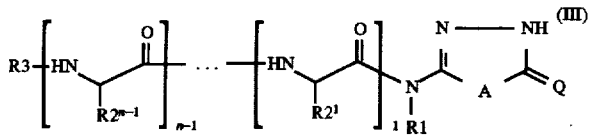

and A are each independently selected from the group consisting of sulfur and oxygen and one of Q and A is sulfur. It is preferred that Q and A are both sulfur.

n is a positive integer and is chosen such that the compound inhibits a matrix metalloproteinase. Preferably, n is an integer from 1 to about 10. More preferably, n is an integer from 1 to about 4.

R1 is selected from the group consisting of —H, lower alkyl and acyl. Lower alkyl includes C1 to about C6 straight or branched chain hydrocarbons. The hydrocarbon can be saturated or can have one or more units of unsaturation. Suitable acyl groups include —CO— (lower alkyl), wherein lower alkyl is defined above. Preferably, R1 is —H.

Each R2 is independently selected from the group consisting of C1–C10 straight or branched alkyl, C1–C10 straight or branched substituted alkyl, C3–C8 cyclic alkyl, substituted C3–C8 cyclic alkyl, C1–C10 straight or branched alkenyl, C1–C10 straight or branched substituted alkenyl, C1–C10 straight or branched alkynyl, C1–C10 straight or branched substituted alkenyl, aryl, substituted aryl, heteroaryl and substituted heteroaryl.

Suitable substituents on a substituted alkyl, alkenyl or alkynyl group include halo, —COOH, —COO(M), —CHO, —OH, —CN, —NO₂, —NH₂, —O(M), —SH, —S(M), —NH(M), —N(M₂), —NH—C(=NH)—NH₂, —NH—C(=NH)—NH(M), lower alkyl, aryl, substituted aryl, heteroaryl and substituted heteroaryl. A substituted alkyl, alkenyl and alkynyl group can optionally have more than one substituent. An alkyl, alkenyl or alkynyl group can also be completely substituted, e.g. perfluorinated. An alkenyl or alkynyl group can have more than one double or triple bond.

M is selected from the group consisting of —X, X—CO—, X—CS—, X—SO₂—, X—O—CO— and X—O—CS—. X is selected from the group consisting of C1–C10 alkyl, C1–C10 substituted alkyl, aryl, substituted aryl, heteroaryl and substituted heteroaryl.

An aryl group can be monocylic (e.g. phenyl) or polycyclic. A polycyclic aromatic group includes fused polycyclic structures, e.g. naphthyl, tetrahydronaphthyl or anthracyl. A polycyclic aromatic group also includes structures with two or more aromatic rings connected by a linker containing one or more single bonds, carbon atoms, and/or heteroatoms, e.g. biphenyl, xanthenyl and fluorenyl. Suitable aryl substituents include halo, —COOH, —COO(M), —CHO, —OH, —CN, —NO₂, —NH₂, —O(M), —SH, —S(M), —NH(M), —N(M₂), aryl, substituted aryl heteroaryl and substituted heteroaryl. M is as defined above. A substituted aryl group can optionally have more than one substituent.

Suitable heteroaryl groups include monocyclic or polycyclic aromatic groups containing one or more heteroatoms such as oxygen, nitrogen or sulfur. Suitable monocyclic heterocyclic groups include imidazolyl, thienyl, pyridyl, furanyl, oxazoyl, pyrollyl, pyrimidinyl, furanyl, pyrazolyl, pyrrolyl, thiazolyl and the like. A polycyclic heteroaryl group includes fused structures such as quinonyl, indoyl, benzimidazoyl, benzothiazolyl, benzothiophenyl, benzofuranyl and benzopyranyl. A polycyclic heteroaromatic group can also include structures with a heteroaromatic ring and one or more aromatic or heteroaromatic rings connected by a linker containing one or more single bonds. Examples include phenylthienyl, thienylthienyl, phenylfuranyl, phenyloxazoyl, thienyloxazoyl and the like. Suitable heteroaryl substituents include halo, —COOH, —COO(alkyl), —OH, —CN, —NO₂, —NH₂, —O(M), —SH, —S(M), —NH(M), —N(M₂), aryl, substituted aryl heteroaryl and substituted heteroaryl. M is as defined above. A substituted heteroaryl group can optionally have more than one substituent.

Preferably, R2 is selected from the group consisting of cyclohexyl, cyclopentyl, (substituted phenyl)-CH₂—, naphthyl, naphthyl-CH₂—, the side chain of a naturally occurring amino acid, and the side chain of a naturally occurring amino acid having a derivatized heteroatom-containing functional group.

A substituted phenyl can have the same substituents as described above for aryl. 2-Fluoro, 3,4-diiodo, 4-nitro 4-benzyloxycarbonylamino 4-dibenzylamino and 4-fluoro are examples. Naphthyl can be either 1-naphthyl or 2-naphthyl.

An amino acid has the general structure NH₂—CHR—COOH, wherein R is the side chain. Naturally occurring amino acids include alanine, valine, leucine, isoleucine, proline, methionine, phenytalanine, homophenylalanine, tryptophan, glycine, serine, homoserine, threonine, cysteine, homocysteine, tyrosine, aminoadipic acid, asparagine, glutamine, aspartic acid, glutamic acid, lysine, histidine, proline, ornithine, homocysteine, hydroxyproline, phenylglycine and tryptophan.

The side chains of many naturally occurring amino acids have heteroatom-containing functional groups which can be derivatized. Examples of such heteroatom-containing functional groups include the thiol of cysteine, the hydroxyl of serine, hydroxyproline and threonine, the carboxylic acid of glutamic acid, adipic acid and aspartic acid, the phenol of tyrosine, the amine of lysine, ornithine, arginine and histidine and the amide of asparagine and glutamine. Suitable derivatizing groups include —X, X—CO—, X—CS—, X—SO₂—, X—O—CO— and X—O—CS—, wherein X is as described above.

Specific examples of suitable derivatizing groups include O-benzyl for tryosyl, seryl, glutamoyl; S-benzyl for cysteinyl; N-trityl for glutamoyl; O-methylene-2-naphthyl for tryosyl; N-trityl for glutamyl; N,N-dibenzyl for glutamyl; ε-N-t-butoxycarbonyl for lysyl; and N-2-phenylethyl for glutamyl.

R3 is an amine derivatizing group such as an amine protecting group. An "amine protecting group" is a functional group which can be bonded to a primary amine, which can be cleaved from the primary amine without causing undesired side reactions in other parts of the molecule and which results in a matrix metalloproteinase inhibitor. Other examples of suitable amine derivatizing groups include X—CO—, X—CS—, X—SO₂—, X—O—CO— and X—O—CS—, wherein X is as defined above.

Preferred amine derivatizing groups include 9-fluorenylmethoxycarbonyl, t-butoxycarbonyl, (4-phenyl) phenylacetyl, 8-quinolinesulfonyl, 2-methylthionicotyl, xanthene-9-carbonyl, hydrocinamoyl, phenylbenzoyl, nonanoyl, (4-benzyloxy)benzoyl, acetyl and (4-(4-t-butylphenylsulfonamino)benzoyl. 4-Phenylbenzoyl, nonanoyl, benzyloxybenzoyl and (4-(4-t-butylphenylsulfonamino)benzoyl are more preferred.

Physiologically active salts of the compound represented by Formula I are also encompassed within the present invention. Physiologically acceptable salts include a hydrochloride salt, a hydrobromide salt and an acetic acid salt.

Specific examples of matrix metalloproteinase inhibitors of the present invention include 5-(N-(9- fluorenylmethoxycarbonyl)valylamino)-1,3,4,-thiadiazole-2-thione, 5-(N-(9-flourenylmethoxycarbonyl) tryptonylamino)-1,3,4-thiadiazole-2-thione, 5-(N-(9-fluorenylmethoxylcarbonyl)leucylamino)-1,3,4-thiadiazole-2-thione, 5-(N-(9-fluorenlylmethoxycarbonyl) methionylamino)-1,3,4-thiadiazole-2-thione, 5-(N-(9-fluorenylmethoxy-carbonyl)homophenylalanylamino)-1,3,4-thiadiazole-2-thione, 5-(N-((4-phenyl)phenylacetyl) valylamino)-1,3,4-thiadiazole-2-thione, 5-(N-benzyloxycarbonyl-(ortho-fluoro)phenylalanylamino)-1,3,4-thiadiazole-2-thione, 5-(N-(8-quinolinesulfonyl) phenylalanyl-valylamino)-1,3,4-thiadiazole-2-thione, 5-(N-(2-methylthionicotyl)phenylalanyl-valylamino)-1,3,4-thiadiazole2-thione, 5-(N-(xanthene-9-carbonyl)glycyl-phenylalanylamino)-1,3,4-thiadiazole-2-thione, 5-(N-hydrocinamoyl-phenylalanyl-valylamino)-1,3,4-thiadiazole-2-thione, 5-(N-(4-phenylbenzoyl)phenylalanyl-valylamino)-1,3,4-thiadiazole-2-thione, 5-(N-nonanoyl-phenylalanyl-valylamino)-1,3,4-thiadiazole-2-thione, 5-(N-(4-phenyl)phenylacetyl-phenylalanyl-valylamino)-1,3,4-thiadiazole-2-thione, 5-(N-(4-benzyloxy)benzoyl-phenylalanyl-valylamino)-1,3,4-thiadiazole-2-thione, 5-(N-(4-phenoxy)benzoyl)-phenylalanyl-valylamino)-1,3,4-thiadiazole-2-thione, 5-(N-(4-(4-t-butylphenylsulfonamino) benzoyl)-phenylalanyl-valylamino)-1,3,4-thiadiazole-2-thione, 5-(N-benzyloxycarbonyl-phenylalanyl-leucylamino)-1,3,4-thiadiazole-2-thione, 5-(N-benzyloxycarbonyl-phenylalanyl-valylamino)-1,3,4-thiadiazole-2-thione, 5-(N-benzyloxycarbonyl-tryptoyl-valylamino)-1,3,4-thiadiazole-2-thione, 5-(N-benzyloxycarbonyl-tryptolyl-phenylalanylamino) 1,3,4-thiadiazole-2-thione, 5-(N-benzyloxycarbonyl-leucylmethionylamino)-1,3,4-thiadiazole-2-thione, 5-(N-benzyloxycarbonyl-(2-(1-naphtyl))alanyl-valylamino)-1,3,4-thiadiazole-2-thione, 5-(N-benzyloxycarbonyl-(2-(2-naphtyl))alanyl-valylamino)-1,3,4-thiadiazole-2-thione, 5-(N-benzyloxycarbonyl-(O-benzyl)tyrosyl-valylamino)-1,3,4-thiadiazole-2-thione, 5-(N-benzyloxycarbonyl-(para-F)phenylalanyl-valylamino)-1,3,4-thiadiazole-2-thione, 5-(N-benzyloxycarbonyl-leucyl-valylamino)-1,3,4-thiadiazole-2-thione, 5-(N-benzyloxycarbonyl-cyclohexylglycyl-valylamino)-1,3,4-thiadiazole-2-thione, 5-(N-benzyloxycarbonyl-isoleucyl-valylamino)-1,3,4-thiadiazole-2-thione, 5-(N-benzyloxycarbonyl-(O-benzyl) glutamoyl-valylamino)-1,3,4-thiadiazole-2-thione, 5-(N-benzyloxycarbonyl-(p-nitro)phenylalanyl-valylamino)-1,3,4-thiadiazole-2-thione, 5-(N-benzyloxycarbonyl-((p-benzyloxycarbonylamino)phenylalanyl)-valylamino)-1,3,4-thiadiazole-2-thione, 5-(N-benzyloxycarbonyl-((3,4-diiodo) phenylalnyl)-valylamino)-1,3,4-thiadiazole-2-thione, 5-(N-benzyloxycarbonyl-((S-benzyl)cysteinyl)-valylamino)-1,3,4-thiadiazole-2-thione, 5-(N-benzyloxycarbonyl-((ortho-flouro)phenyalanyl)-valylamino)-1,3,4-thiadiazole-2-thione, 5-(N-benzyloxycarbonyl-(O-benzyl)seryl)-valylamino)-1,3,4-thiadiazole-2-thione, 5-(N-benzyloxycarbonyl-((N-trityl)glutamyl)-valylamino)-1,3,4-thiadiazole-2-thione, 5-(N-benzyloxycarbonyl-((O-benzyl) tyrosyl)-aminoisobutyroyl amino)-1,3,4-thiadiazole-2-thione, 5-(N-benzyloxycarbonyl-((O-benzyl)tyrosyl)-phenylglycylamino)-1,3,4-thiadiazole-2-thione, 5-(N-benzyloxycarbonyl-((O-methylene-2-naphtyl)tyrosyl)-valylamino)-1,3,4-thiadiazole-2-thione, 5-(N-benzyloxycarbonyl-((O-benzyl)tyrosyl)-glycylamino)-1,3,4-thiadiazole-2-thione, 5-(N-benzyloxycarbonyl-((O-benzyl)tyrosyl-(t-butyl)glycylamino)-1,3,4-thiadiazole-2-thione, 5-(N-benzyloxycarbonyl-((N-trityl)glutamyl)-phenylglycylamino)-1,3,4-thiadiazole-2-thione, 5-(N-benzyloxycarbonyl-((O-benzyl)tyrosyl)-cyclohexylglycylamino)-1,3,4-thiadiazole-2-thione, 5-(N-t-butyloxycarbonyl-((O-benzyl)tyrosyl)-phenylglycylamino)-1,3,4-thiadiazole-2-thione, 5-(N-benzyloxycarbonyl-((N,N-dibenzyl)glutamyl)-phenylglycylamino)-1,3,4-thiadiazole-2-thione, 5-(N-benzyloxycarbonyl-((p-N,N-dibenzylamino) phenylalanyl)-phenylglycylamino)-1,3,4-thiadiazole-2-thione, 5-(N-benzyloxycarbonyl-((O-benzyl)tyrosyl)-luecylamino)-1,3,4-thiadiazole-2-thione, 5-(N-benzyloxycarbonyl-(N-2-phenylethyl)glutamyl-phenylgycylamino)-1,3,4-thiadiazole-2-thione, 5-(N-benzyloxycarbonyl-phenylalanyl-leucyl-tryptonylamino)-1,3,4-thiadiazole-2-thione, 5-(N-benzyloxycarbonyl-phenylalanyl-valyl-tryptonylamino)-1,3,4-thiadiazole-2-thione, 5-(N-benzyloxycarbonyl-phenylalanyl-tryptonyl-valylamino)-1,3,4-thiadiazole-2-thione, 5-(N-benzyloxycarbonyl-lysyl(N-epsilon-t-butyloxycarbonyl)-tyrosyl(O-benzyl)-phenylglycylamino)-1,3,4-thiadiazole-2-thione.

The compounds of the present invention are synthesized by coupling 5-amino-1,3,4-thiadiazole-2-thione with an N-terminus protected amino acid or oligopeptide. 5-Amino-1,3,4-thiadiazole is prepared according to known methods (Cho and Kim, *J. Heterocyclic Chem.*, 30:397 (1993)). Methods of protecting the N-terminus of amino acids or oligopeptides are also well known (see Greene and Wuts, "Protecting Groups in Organic Synthesis", John Wiley and Sons, 1991). Coupling is carried out by known methods of peptide synthesis, for example by dicyclohexylcarbodiimide mediated coupling in the presence of 1-hydroxybenzotriazole (see Examples 1–36). Additional amino acids or oligopeptides can be added to the N-terminus by cleavage of the amino protecting group and then performing a second coupling with an N-terminus protected amino acid or oligopeptide. The process can be repeated as often as required to synthesize a thiadiazole having an oligopeptide of desired length and sequence which is bound to the 5-amino group of the thiadiazole.

Another embodiment of the present invention is a method of inhibiting a matrix metalloproteinase. The method comprises contacting the matrix metalloproteinase with an inhibitory amount of a compound represented by Structural Formula II.

Matrix metalloproteinases are a class of zinc-dependent, proteolytic enzymes which bind and cleave peptides having a specific amino acid sequence. Examples of enzymes in this class of proteins include stromelysin (MMP-3), human fibroblast collagenase (MMP-1), human 72-kDalton gelatinase (MMP-2), human neutrophil collagenase (MMP-8), human 92-kDa gelatinase (MMP-9) and matrilysin (MMP-10).

An inhibitory amount of the compound is the quantity of the compound which results in reduced cleavage of matrix metalloproteinase substrates in the presence of the compound compared with in its absence. An inhibitory amount depends on several factors, including the inhibitor used, the pH of the solution, other consituents in the solution and temperature. The skilled artisan is able to vary the amount of inhibitor used, depending on the application. Typically, a concentration from about 1 nanomolar or less to about 10,000 nanomolar is used, preferably about 1 nanomolar or less to about 1000 nanomolar and more preferably about 1 nanomolar or less to about 500 nanomolar.

Specific examples where at least one matrix metalloproteinase is inhibited in vitro with an amino acid amide of 5-amino-1,3,4-thiadiazole-2-thiol are provided in Examples 37–40. In these examples amino acid amides of 5-amino-1, 3,4-thiadiazole-2-thiols are tested in vitro for their ability to inhibit stromelysin, 92 kDa human gelatinase, 72 kDa human gelatinase and human neutrophil collagenase. Inhibition data are provided in Tables I–IV as the $IC_{50}$.

Another embodiment of the present invention is a method of treating an individual with a disease that can be ameliorated by inhibiting at least one matrix metalloproteinase enzyme. The method comprises administering a therapeutically effective amount of a compound having the structure of Formula II.

The method can also be used to treat an animal with a disease that can be ameliorated by inhibiting at least one matrix metallproteinase enzyme. Animals which can be treated by this method include, dogs, cats, farm animals, guinea pigs and the like.

A disease is "ameliorated" when the development or progression of a disease process associated with the disease is slowed, arrested or reversed as a result of a treatment. For example, osteoarthritis and rheumatoid arthritis can be ameliorated by slowing the cartilage degradation that occurs as a result of the disease. Alternatively, "amelioration" can include alleviating pain and inflammation in the afflicted joints of an individual with osteoarthritis or rheumatoid arthritis. Another example of disease "amelioration" includes increasing the life expectancy of individual with the disease, for example an individual with cancer, or increasing the quality of life of the individual, e.g. by increasing the mobility of an individual with osteoarthritis.

Specific examples of where a disease process is ameliorated by the administration of an amino acid amide of 5-amino-1,3,4-thiadiazole-2-thione are provided in Example 41. In these examples compounds are tested for their ability to inhibit the degradation of extracellular matrix in tissue culture. Extracellular cartilage degradation occurs in osteoarthritis and rheumatoid arthritis. Inhibition data for the compounds tested in the tissue culture assay are provided in Table V as the percent inhibition of cartilage degradation at the given concentration.

Other diseases which can be treated with amino acid amides of 5-amino-1,3,4-thiadiazoles include tumor cell metastasis in cancer, ulcerations and infections resulting from periodontal disease or epidermoysis bullosa. In addition, these compounds can be used to treat inflammation in diseases in which inflammation is caused by the overactivity of at least one matrix metalloproteinase enzyme.

A therapeutically effective amount of the compound is the quantity which brings about an amelioration of the disease without causing unacceptable side effects. The amount of compound which is administered to the individual or animal depends on many factors, including the age, sex, weight and general health of the individual as well the severity of the disease with which the individual is afflicted. The skilled artisan will be able to vary the amount of compound administered to the individual, depending on these and other factors. Typically, a therapeutically effective amount ranges from about 0.1 mg/kg per day or less to about 100 mg/kg per day, preferably from about 0.1 mg/kg per day or less to about 20.0 mg/kg per day.

The compound can be administered orally, for example, in capsules, suspensions or tablets. Other modes of administration which can be used include systemic administration, such as by intramuscular, intravenous, subcutaneous, or intraperitoneal injection. When treating osteoarthritis, the compound is preferably administered intraarticularly into the afflicted joint, for example by intraarticular injection.

The compound can be administered to the individual in conjunction with an acceptable pharmaceutical carrier as part of a pharmaceutical composition for treating osteoarthritis. Suitable pharmaceutical carriers may contain inert ingredients which do not interact with the compound. Standard pharmaceutical formulation techniques may be employed such as those described in Remington's Pharmaceutical Sciences, Mack Publishing Company, Easton, Pa. Suitable pharmaceutical carriers for intraarticular and other parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin of cyclodextran) are known in the art (Baker, et al., "Controlled Release of Biological Active Agents", John Wiley and Sons, 1986).

In another embodiment of the present invention the composition, in addition to the compound, additionally comprises another pharmacologically active agent. Osteoarthritis and rheumatoid arthritis are characterized by pain in the afflicted joints. Individuals with cancer often suffer from pain resulting from tumors contacting organs or other body tissue. Consequently, when treating osteoarthritis, rheumatoid arthritis or cancer it can be advantageous to co-administer the compound with an analgesic or other pain-killing medication. Suitable analgesics include acetominophen, acetyl salicylic acid and the like. Osteoarthritis and rheumatoid arthritis are also characterized by inflammation in the afflicted joints. Consequently, it can be advantageous to administer the compound together with an anti-inflammatory agent such as a non-steroidal anti-inflammatory drug or steroid (e.g. triamcinolone, amcinonide and the like) when treating osteoarthritis and rheumatoid arthritis.

Amino acid amides of 1,3,4-thiadiazole-2-thiones have useful applications in vitro. Because matrix metalloproteinases have protease activity and are present in a wide variety of tissue, the isolation of useful tissue and biological fluids is often hampered by undesired proteolysis of useful proteins by these enzymes. Destruction of useful tissue and proteins by these matrix metalloproteinases can be prevented by adding an inhibitory amount of the thiadiazoles of the present invention. Matrix metalloproteinases, as discussed earlier, are involved in a wide variety of disease processes. Consequently, inhibitors of matrix metalloproteinase are useful in disease research, for example to study the structure activity requirements for designing new and better inhibitors of these enzymes.

An amino acid amide of a 1,3,4-thiadiazole-2-thione can be coupled to a radiolabel, such as the $Te^{99}$ or $I^{131}$ scintigraphic labels, using standard coupling methods. A radiolabeled amino acid amide of a 1,3,4-thiadiazole-2-thione is then administered to a subject to determine any locations of excess amounts of one or more metalloproteinase in vivo. The ability of a thiadiazole compound to selectively bind to a metalloproteinase is then used to map the distribution of these enzymes in situ. The techniques can also, of course, be employed in the histological procedures, and the labeled compounds can be used in competitive immunoassays.

At least one amino acid amide of a 1,3,4-thiadiazole-2-thione can also be coupled to a solid support, such as a separation membrane, a chromatographic support, for example agarose, sepharose, polyacrylamide, or the like, or to a microtiter plate to provide an affinity support which is useful in purifying a matrix metalloproteinase enzyme. The selective binding of the matrix metalloproteinase to the thiadiazole compound permits the adsorption of the desired enzyme and its subsequent elution using, for example, altered ionic strength and/or pH conditions.

The invention will now be further and specifically described by the following examples.

EXAMPLE 1

Synthesis of 5-(N-(9-fluorenylmethoxycarbonyl) tryptonylamino)-1,3,4-thiadiazole-2-thione Dicyclohexylcarbodiimide (0.42 grams) was dissolved in 5 mL of anhydrous dimethylformamide (DMF), followed by the addition of N-fluorenylmethoxycarbonyl-trytophan (N-(9-fluorenylmethoxycarbonyl is referred to as "fmoc") (0.85 grams) and 1-hydroxybenzotriazole (HBT) (0.36 grams). The solution was kept at room temperature until dicyclohexylurea precipitation was completed (about 40 minutes).

5-Amino-1,3,4-thiadiazole-2-thione (0.3 grams) was added and the reaction mixture was allowed to stir for 48 hours. An excess of ethyl acetate was the added (100 mL) and the resulting solution was washed three times with 5% aqueous sodium bicarbonate, 10% aqueous citric acid and water. The ethyl acetate layer was dried with magnesium sulfate and evaporated to dryness. The resulting oily residue was recrystallized from ethanol-pentane. The resulting white solid was filtered off and air-dried. M.P. 162°–163° C. NMR spectrum ($d_6$-DMSO) 14.05 (s, 1H), 12.75 (s, 1H), 10.85 (s, 1H), (6.9–8.0, m, 13 H; NH+aromatics), 4.5 (m,1H), 4.1 (m, 3H), 2.9–3.5 (m, 2H).

EXAMPLE 2

Synthesis of 5-(N-(9-fluorenylmethoxycarbonyl) valylamino)-1,3,4-thiadiazole-2-thione Fmoc-Valine (0.68 grams), 1-hydroxybenzotriazole (0.36 grams), dicyclohexylcarbodiimide (0.42 grams) and 5-amino-1,3,4-thiadiazole-2-thione (0.4 grams) were reacted according to the procedures described in Example 1. The resulting product was recrystallized from ethanol-pentane. M.P. 141°–144° C. NMR spectrum ($d_6$-DMSO) 14.06 (s, 1H), 12.56 (s,1H), 8.00–7.60;7.5–7.2 (m, 9H; NH+aromatics) 4.4–4.0 (m, 4H) 2.2–2.0 (m, 1H), 0.98 (bs, 6H).

EXAMPLE 3

Synthesis of 5-(N- benzyloxycarbonyl-tryptonylamino)-1,3,4-thiadiazole-2-thione

N-Benzyloxycarbonyl -Tryptophan (1.7 grams), 1-hydroxybenzotriazole (1 grams), dicyclohexylcarbodiimide (1.1 grams) and 5-amino-1,3,4-thiadiazole-2-thione (2.5 grams) were reacted according to the procedure described in Example 1. The resulting product was recrystallized from ethanol/ethyl acetate/pentane to give a white powder. M.P. 128°–132° C. NMR spectrum ($d_6$-DMSO) 14.08 (s, 1H), 12.77 (s, 1H), 10.84 (s, 1H), 7.8–7.6, 7.4–6.9 (M, 11H, NH+aromatics), 4.95 (s, 2H), 4.5 (m, 1H) 3.3–2.9 (m, 2H).

EXAMPLE 4

Synthesis of 5-(N-9-fluorenylmethoxycarbonyl) methionylamino)-1,3,4-thiadiazole-2-thione Fmoc-Methionine (0.371 grams), 1-hydroxybenzotriazole (0.2 grams), dicyclohexylcarbodiimide (0.21 grams) and 5-amino-1,3,4-thiadiazole-2-thione (0.25 grams) were reacted according to the procedure described in Example 1. The resulting product was recrystallized from ethanol/ petroleum ether to give the product as white powder. M.P. 166°–167° C. NMR spectrum (d6-DMSO) 14.1 (s, 1H), 12.62 (s, 1H), 7.9–7.2 (m, 9H, NH+aromatics), 4.4–4.1 (M, 4H), 2.1 (s, 3H), 2.2–1.8 (m,4H).

EXAMPLE 5

Synthesis of 5-(N-(9-flourenylmethoxycarbonyl) homophenylalanylamino)-1,3,4-thiadiazole-2-thione Fmoc-phenylalanine (0.8 grams), 1-hydroxybenzotriazole (0.38 grams), dicyclohexylcarbodiimide (0.4 grams) and 5-amino-1,3,4-thiadiazole-2-thione (0.4 grams) were reacted according to the procedure described in Example 1. The resulting product was recrystallized from ethanol/ pentane to give a white powder. M.P. 186°–187° C. NMR spectrum ($d_6$-DMSO) 14.08 (s, 1H), 12.6 (s, 1H), 8.00–7.1 (m, 14 H, NH+aromatics), 4.4–4.1 (m, 4H), 2.8–2.3 (m, 2H), 2.1–1.8 (m, 2H).

EXAMPLE 6

Synthesis of 5-(N-((4-phenyl)phenylacetyl) valylamino)-1,3,4-thiadiazole-2-thione ((4-Phenyl)phenylacetyl)-valine (0.98 grams), 1-hydroxybenzotriazole (0.6 grams), dicyclohexylcarbodiimide (0.64 grams) and 5-amino-1,3,4-thiadiazole-2-thione (1.2 grams) were reacted according to the procedure described in Example 1. The resulting product was recrystallized from ethanol/pentane to give a white solid. M.P. 232°–236° C. NMR spectrum ($d_6$-DMSO) 14.1 (s, 1H), 12.6 (s, 1H), 8.42 (d, 1H, NH), 7.8–7.2 (m, 9H, aromatics), 4.35 (m, 1H), 3.75–3.4 (m, 2H), 2.05 (m, 1H), 0.9 (d, 6H).

EXAMPLE 7

Synthesis of 5-(N-benzyloxycarbonyl-phenylalanyl-valylamino)-1,3,4-thiadiazole-2-thione Cbz-Phenylalanine-valine-OH (0.8 grams), 1-hydroxybenzotriazole (0.35 grams), dicyclohexylcarbodiimide (0.41 grams) and 5-amino-1,3,4-thiadiazole-2-thione (0.9 grams) were reacted according to the procedure described in Example 1. The resulting product was recrystallized from ethyl acetate/petroleum ether to give a white solid. M.P. 170°–174° C. NMR spectrum ($d_6$-DMSO) 14.1 (s, 1H), 12.6 (s, 1H), 8.22 (d, 1H), 7.52 (d, 1H), 7.1–7.4 (m, 10 H, aromatics), 4.95 (s, 2H), 4.38 (m, 2H), 2.9 (m, 1H), 2.75 (m, 1H), 2.05 (m, 1H), 0.9 (bs, 6H).

EXAMPLE 8

Synthesis of 5-(N-(4-(4-t-Butylphenylsulfonylamino)benzoyl)-phenylalanyl-valylamino)-1,3,4-thiadiazole-2-thione (4-(4-t-Butylphenylsulfonylamino)benzoyl)-phenylalanine-valine, (0.48 grams) 1-hydroxybenzotriazole (0.15 grams), dicyclohexylcarbodiimide (0.17 grams) and 5-amino-1,3,4-thiadiazole-2-thione (0.5 grams) were reacted according to the procedure described in Example 1. The resulting product was recrystallized from ethanol/ pentane to give a white solid. M.P. 140°–144° C. NMR spectrum ($d_6$-DMSO) 14.1 (s, 1H), 12.6,12.5 (s,s, 1H), 10.8 (s, 1H), 8.6–8.2, 7.8–7.4, 7.4–7.0 (m, 15 H, NM+aromatics), 4.8 (m, 1H), 4.35 (m, 1H), 3.5–2.8 (m, 2H), 2.05 (m, 1H), 1.2 (s, 9H), 0.85 (bs, 6H).

EXAMPLE 9

Synthesis of 5-(N-benzyloxycarbonyl-(2-(1-naphthyl))alanyl-valylamino)-1,3,4-thiadiazole-2-thione tert-Butoxycarbonyl-1-naphthalanine (Boc-1-Naphthalanine) (500 mg, 1.6 mmol), valine methyl ester hydrochloride (292 mg, 1.1 equivalent), diisopropylethylamine (305 mL, 1.1 eq) and 1-hydroxybenzotriazole (242 mg, 1.0 eq) were added to 15 mL of $CH_2Cl_2$. The solution was allowed to equilibrate 15 minutes at room temperature, followed by the addition of dicyclohexylcarbodiimide (360 mg, 1.1 eq). The reaction was then stirred at room temperature overnight. The precipitated dicyclohexylurea was removed by filtration. The resulting solution was washed with 5% HCl (2×30 mL), 10% $NaHCO_3$ (2×30 mL) and brine (2×30 mL). The organic layer was then dried ($Na_2SO_4$) and evaporated to dryness. The resulting material was used without further purification.

Deprotection of the Boc group was carried out as reported in literature (Bodanszky and Bodanszky "The Practice of Peptide Synthesis") using neat trifluoroacetic acid at 0° for 15 minutes. Excess trifluoroacetic acid was removed under reduced pressure and the trifluoroacetic acid salt was dried overnight over a bed of NaOH.

The free N-terminus was acylated with benzylchloroformate (Cbz-Cl) by dissolving the trifluoroacetic acid salt in $CH_2Cl_2$ at 0°. Diisopropylethylamine (695 mL, 2.5 eq) was added, followed by the dropwise addition of benzyl chloroformate (250 mL, 1.2 eq). The reaction was then allowed to warm to room temperature over 1 hour. The reaction mixture was washed with 5% HCl (2×30 mL), 10% $NaHCO_3$ (2×30 mL) and brine (2×30 mL). The organic layer was dried ($Na_2SO_4$), evaporated to dryness, and used without further purification.

Saponification of the methyl ester was accomplished by dissolving the ester in 2 mL methanol (MeOH), adding 2 mL of 1N NaOH and allowing the reaction to stir at room temperature. The reaction is conveniently monitored by TLC and complete reaction is usually seen after about 1 hour. The MeOH:$H_2O$ mix is diluted out with $H_2O$ and washed with ether (2×15 mL). The aqueous phase is carefully acidified (1N HCl) and washed with ethyl acetate (5×10 mL). The organic layers are combined, washed once with 5% HCl and brine, dried ($Na_2SO_4$) and evaporated to dryness. TLC showed one spot and this was used without further purification. Yield of the crude acid was 500 mg (69%). Coupling with the thiadiazole (5-amino-1,3,4-thiadiazole-2-thiol) was accomplished by dissolving the above acid in 5 mL DMF under a stream of argon. The thiadiazole, (330 mg, 2.2 mmol, 2 eq), 1-hydroxybenzotriazole (HOBt) (180 mg) and dicyclohexylcarbodiimide (253 mg, 1.1 eq) were then added to the reaction mixture. The reaction mixture was thoroughly flushed with argon, stoppered tightly, and allowed to stir at room temperature 72 hrs. Workup was as described in Examples 1–3.

An analytically pure sample was obtained by preparative TLC using $CH_2Cl_2$:MeOH (95:5), $R_f$=0.47. Melting point 176.8°–180° C. $^1$H-NMR ($d_6$-DMSO, internal ref.) 14.1 (br s, NH thiadiazole) 12.5 (br s, NH amide thiadiazole) 8.4–7.0 (m, 14H, aromatic+amides) 4.9 (s, 2H, $CH_2$ CBZ) 4.5 (m, 1H, chiral) 4.3 (m, 1H, chiral) 3.5 (m, 2H, $CH_2$ benzylic) 2.0 (m, 1H, CH valine) 0.8 (m, 6H, $CH_3$).

EXAMPLE 10

Synthesis of 5-(N-benzyloxycarbonyl-(2-(2-naphthyl)alanyl-valylamino)-1,3,4-thiadiazole-2-thione The synthesis was carried out according to the procedure described in Example 9, except that Boc-2-naphthalanine was used in place of Boc-naphthalanine.

An analytically pure sample was obtained by preparative TLC using $CH_2Cl_2$:MeOH (95:5), $R_f$=0.41. Melting point 125.2°–132.5° C. $^1$H-NMR ($d_6$-DMSO, int. std.) 14.1 (br s, ½H, NH thiadiazole) 12.6 (br s, ½H, NH amide thiadiazole) 8.3 (d, 14H, amide) 7.9–7.0 (m, 13H, aromatic +1 amide) 4.9 (s, 2H, $CH_2$ CBZ) 4.5 (m, 1H, chiral) 4.3 (m, 1H, chiral) 0.8 (m, 6H, $CH_3$).

EXAMPLE 11

Synthesis of 5-(N-benzyloxycarbnyl-(O-benzyl)tyrosyl-valylamino)-1,3,4-thiadiazole-2-thione N-Benzyloxycarbonyl-(O-benzyl)tyrosine (6.35, 1.5 mmol), valine methyl ester hydrochloride (250 mg, 1.1 eq), diisopropylethylamine (260 mL, 1.1 eq) and HOBt (230 mg) were added to 15 mL of DMF. The reaction was then allowed to equilibrate for 15 minutes, followed by the addition of dicyclohexylcarbodiimide (340 mg 1.1 eq). The reaction was allowed to stir overnight at room temperature, after which the precipitated dicyclohexylurea was filtered off. The supernatant was extracted with 5% HCl (2×30 mL), 10% $NaHCO_3$ (2×30 mL) and brine (2×30 mL). The organic layer was dried, ($Na_2SO_4$) evaporated to dryness and used without further purification.

Saponification of the methyl ester was accomplished by dissolving the ester in 2 mL methanol and adding 2 mL of 1N NaOH and allowing the reaction to stir at room temperature. The reaction is conveniently monitored by TLC and complete reaction is usually seen after about 1 hour. The methanol $H_2O$ mixture is diluted out with $H_2O$ and washed with ether (2×15 mL). The aqueous phase is carefully acidified (1N HCl) and washed with ethyl acetate (5×10 mL). The organic layer is combined, washed once with 5% HCl and brine, dried ($Na_2SO_4$) and evaporated to dryness. TLC showed one spot. This product was used without further purification. Yield of the crude acid was 530 mg (70%).

Coupling with the 5-amino-1,3,4-thiadiazole-2-thiole was performed as described in Example 9.

An analytical sample was prepared by preparative TLC using $CH_2Cl_2$:MeOH (95:5), $R_f$=0.39. Melting point 111.7°–119.4° C. $^1$H-NMR ($d_6$-DMSO, int. std.) 14.1 (br s, ½H, NH thiadiazole) 12.6 (br s, ½H, NH amide thiadiazole) 8.2 (d, 1H, amide) 7.6–6.8 (m, 15H, aromatic+1 amide) 5.1 (s, 2H, $CH_2$ benzyl) 4.9 (s, 2H, $CH_2$ CBZ) 4.3 (m, 2H, 2×chiral) 0.9 (m, 6H, $CH_3$).

EXAMPLE 12

Synthesis of 5-(N-benzyloxycarbonyl-(1,2,3,4-tetrahydroisoquinoline-3-carboxy)-valylamino)-1,3,4-thiadiazole2-thione The synthesis was carried out as described in Example 9 except that Boc-(1,2,3,4-tetrahydroisoquinoline-3-carboxylic acid) (Advanced ChemTech., Louisville, Ky.) was used in place of Boc-1-napthalanine.

An analytical sample was prepared by preparative TLC using $CH_2Cl_2$:MeOH (95:5), $R_f$=0.34. Melting point 128.5°–133.5° C. $^1$H-NMR ($d_6$-DMSO, int. std.) 14.1 (br s, ½H, NH thiadiazole) 12.5 (br s, ½H, NH amide thiadiazole) 8.1 (d, 1H, amide valine) 7.5–7.1 (m, 9H, aromatic) 5.2 (m, 2H, $CH_2$ CBZ) 4.6 (m, 3H, tetradyroisoquinoline) 4.2 (q, 1H, chiral) 3.1 (m, 2H, tetrahydroisoquinoline) 0.7 (m, 6H, $CH_3$).

EXAMPLE 13

Synthesis of 5-(N-benzyloxycarbonyl(para-F)phenylalanyl-valylamino)-1,3,4-thiadiazole-2-thione The synthesis was carried out as described in Example 9 except that Boc-4-fluoro-phenylalanine was used in place of Boc-1-napthalanine.

An analytical sample was prepared by preparative TLC using CH$_2$Cl$_2$:MeOH (95:5), R$_f$=0.26. Melting point 127.6°–130.2° C. $^1$H-NMR (d$_6$-DMSO, int. std.) 14.1 (br s, ½H, NH thiadiazole) 12.6 (br s, ½H, NH amide thiadiazole) 8.2 (d, 1H, amide valine) 7.5 (d, 1H, amide) 7.4–6.9 (m, 9H, aromatic) 4.9 (s, 2H, CH$_2$, CBZ) 4.3 (m, 2H, 2×chiral) 2.9–2.7 (m, 2H, CH$_2$, phenyl) 2.0 (app q, 1H, CH val, app J=0.9 (app s, 6H, CH$_3$).

EXAMPLE 14

Synthesis of 5-(N-benzyloxycarbonyl-Cyclohexylglycyl-valylamino)-1,3,4-thiadiazole-2-thione Synthesis of the N-benzyloxycarbonyl-cyclohexylglycine (Cbz-CHG) was accomplished using Schotten-Baumann conditions (Bodanszky, "Principles of Peptide Synthesis"). (L)-Cyclohexylglycine (Advanced ChemTech, Louisville, Ky.) was dissolved in a water/dioxane mixture with benzyl chloroformate (Cbz-Cl). 5N NaOH was used to maintain the pH at about 10. After the reaction was complete, the mixture was adjusted to pH 7, concentrated to half-volume, diluted with water, acidified to pH 3 and extracted with ethyl acetate. The combined organic washes were dried (Na$_2$SO$_4$) and evaporated to dryness. The crude product, Cbz-CHG, was used without further purification. The procedure described in Example 11, using Cbz-CHG in place of N-benzyloxycarbonyl-(O-benzyl)tyrosine, was used to complete the synthesis.

An analytical sample was prepared by preparative TLC using CH$_2$Cl$_2$:MeOH (95:5), R$_f$=0.25. Melting point 190°–193.8° C. $^1$H-NMR (d$_6$-DMSO, int. std.) 14.1 (s, ⅓H, NH thiadiazole) 12.5 (s, ⅓H, NH amide thiadiazole) 8.1 (d, 1H, amide) 7.3 (apps, 6H, aromatic+1 amide) 5.0 (s, 2H, CH$_2$ CBZ) 4.3 (q, 1H, chiral) 3.9 (m, 1H, chiral) 3.6 (br m, 6H, cyclohexane) 1.0 (br m, 11H, cyclohexane+CH$_3$).

EXAMPLE 15

Synthesis of 5-(benzyloxycarbonyl-(p-nitro) phenylalanyl-valylamino)-1,3,4-thiadiazole-2-thione Synthesis of the requisite N-benzyloxycarbonyl-(p-nitro) phenylalanine was accomplished using the Schotten-Baumann conditions (Bodanszky, "Principles of Peptide Synthesis"). (L)-4—NO$_2$-Phenylalanine (Bachem Bioscience, Inc., King of Prussia, PA) was dissolved in a water/dioxane mixture with Cbz-Cl 5N NaOH was used to maintain the pH at about 10. After the reaction was complete, the mixture was adjusted to pH 7, concentrated to half-volume, diluted with water, acidified to pH 3 and extracted with ethyl acetate. The combined organic washes were dried (Na$_2$SO$_4$) and evaporated to dryness. The crude product, Cbz-4-nitrophenylalanine, was used without further purification.

The procedure described in Example 11, using Cbz-4-nitrophenylalanine in place of Cbz-(O-benzyl)tyrosine, was used to complete the synthesis.

An analytical sample was prepared by preparative TLC using CH$_2$Cl$_2$:MeOH (95:5), R$_f$=0.22. Melting point 137.6°–51.5° C. $^1$H-NMR (d$_6$-DMSO, int. std.) 14.1 (br s, ½H, NH thiadiazole) 12.6 (br s, ½H, NH amide thiadiazole) 8.3 (d, 1H, amide) 8.1 (d 2H, aromatic α to NO$_2$) 7.6=7.2 (m 8H, aromatic+1 amide) 4.9 (s, 2H, CH$_2$ CBZ) 4.4 (m, 2H, 2×chiral) 2.0 (m, 1H, CH valine) 0.9 (app s, 6H, CH$_3$).

EXAMPLE 16

Synthesis of 5-(N-benzyloxycarbonyl-((p-benzyloxycarbonylamino)phenyl-alanyl)-valylamino)-1,3,4-thiadiazole-2-thione N-Benzyloxycarbonyl-(p- benzyloxycarbonylamino)-phenylalanine compound was prepared using Schotten-Baumann conditions (Bodanszky, "Principles of Peptide Synthesis") as described in Examples 14 and 15 starting with (L)-4-amino-phenylalanine (Bachem Bioscience, King of Prussia, Pa.) and using two equivalents of Cbz-Cl. The procedure described in Example 11, using N-benzyloxycarbonyl-(p-benzyloxycarbonylamino) phenylalanine in place of N-benzyloxycarbonyl-(O-benzyl) tyrosine, was used to complete the synthesis.

An analytical sample was prepared by preparative TLC using CH$_2$Cl$_2$:MeOH (95:5), R$_f$=0.22. Melting point 195.2°–203.4° C. $^1$H-NMR (d$_6$-DMSO, int. std.) 14.1 (br s, ½H, NH thiadiazole) 12.6 (br s, ½H, NH amide thiadiazole) 9.7(d, 1H, amide) 8.2 (d 1H, amide) 7.3 (m 15H, aromatic+ amide) 5.2 (s, 2H, CH$_2$ CBZ on para-amino group) 4.9 (s, 2H, CH$_2$-CBZ on α nitrogen) 4.3 (m, 2H, 2×chiral) 2.0 (app s, 1H, CH valine) 0.8 (m, 6H, CH$_3$).

EXAMPLE 17

Synthesis of 5-(N-benzyloxycarbonyl-(O-benzyl) glutamoyl-valylamino)-1,3,4-thiadiazole-2-thione (N-t-butoxycarbonyl)valine (750 mg, 3.4 mmol) was added to 5 mL of anhydrous DMF in a reaction flask that had been flushed with argon. 5-Amino-1,3,4-thiadiazole-2-thiol (920 mg, 2 equivalents), HOBt (530 mg) and dicyclohexylcarbodiimide (782 mg, 1.1 equivalents) were then added. The reaction vessel was tightly stoppered and the reaction allowed to stir at room temperature for 72 hours. The reaction mixture was then diluted with ethyl acetate (50 mL). The precipitated dicyclohexylurea was filtered off and the supernatant washed with 10% citric acid (3×20 mL), 10% NaHCO$_3$ (3×20 mL) and brine (3×20 mL). The organic layer was dried (Na2SO$_4$) and evaporated to dryness. The crude product was crystallized from CH$_2$Cl$_2$/petroleum ether (50°–110° C.). Yield of the Boc-Val-X was 670 mg, 59%. Deprotection of the t-butoxycarbonyl group was preformed as reported in literature (Bodanszky and Bodanszky "The Practice of Peptide Synthesis") by stirring in 4N HCl:dioxane overnight under argon. The solvent was removed under reduced pressure and the hydrochloride salt was dried overnight over a bed of NaOH. The product was used without further purification.

N-Benzyloxycarbonyl-(O-benzyl)glutamate (200 mg, 0.54 mmol) was added to 5 mL of anhydrous DMF under argon. To this mixture was added 5-valyamino-1,3,4-thiadiazole-2-thione (144 mg, 1.1 eq), diisopropylethylamine (DIEA) (100 mL, 1.1 eq), HOBt (82 mg) and dicyclohexylcarbodiimide (122 mg, 1.1 eq). The reaction vessel was flushed with argon, tightly stoppered and allowed to stir overnight at room temperature. After diluting the reaction mixture with ethyl acetate (50 mL), the dicyclohexylurea was filtered off. The supernatant was then washed 10% citric acid (3×20 mL), 10% NaHCO$_3$ (3×20 mL) and brine (3×20 mL). The organic layer was dried (Na$_2$SO$_4$) and evaporated to dryness.

An analytical sample was prepared by preparative TLC using CH$_2$Cl$_2$:MeOH (95:5), R$_f$=0.24. Melting point 97.6°–102.3° C. $^1$H-NMR (d$_6$-DMSO, int. std.) 14.1 (br s, 1H, NH thiadiazole) 12.7 (br s, 1H, NH amide thiadiazole) 8.2 (d, 1H, amide) 7.5 (d 1H, amide) 7.4 (app s, 10H, aromatic) 5.1 (s, 2H, CH$_2$ benzyl) 5.0 (s, 2H, CH$_2$ CBZ) 4.3 (t, 1H, chiral, J+) 4.1 (m, 1H, chiral) 1.9 (m, 4H, CH$_2$ Glu 0.9 (app s, 6H, CH$_3$).

EXAMPLE 18

Synthesis of 5-(N-benzyloxycarbonyl-((3,4-diiodo) phenylalanyl)-valylamino)-1,3,4-thiadiazole-2-thione This compound was prepared according to the procedure described in Example 9, using Boc-(3,5-diiodo)-phenylalanine in place of Boc-1-napthalanine.

An analytical sample was prepared by preparative TLC using $CH_2Cl_2$:MeOH (95:5), $R_f$=0.38. Melting point 178.4°–181.2° C. $^1$H-NMR ($d_6$-DMSO, int. std.) 14.1 (br s, 1H, NH thiadiazole) 12.6 (br s, 1H, NH amide thiadiazole) 9.3 (s, 1G, OH Tyr) 8.3 (s 1H, amide) 7.7 (s, 2H, aromatic Tyr) 7.5 (d, 1H, amide) 7.2 (m, 5H, aromatic CBZ) 4.9 (s, 2H, $CH_2$CBZ) 4.3 (m, 2H, 2×chiral) 2.0 (br d, 1H, CH Val) 0.9 (app s, 6H, $CH_3$).

EXAMPLE 19

Synthesis of 5-(N-benzyloxycarbonyl-(O-benzyl)seryl-valylamino)-1,3,4-thiadiazole-2-thione This compound was prepared according the method described in Example 11 using N-benzyloxycarbonyl-(O-benzyl)serine in place of N-benzyloxycarbonyl-(O-benzyltyrosine).

An analytical sample was prepared by preparative TLC using $CH_2Cl_2$:MeOH (95:5), $R_f$=0.33. Melting point 122.6°–128.9° C. $^1$H-NMR ($d_6$-DMSO, int. std.) 14.1 (br s, 1H, NH thiadiazole) 12.5 (br s, NH amide thiadiazole) 8.2 (d, 1H, amide) 7.3 (m 10H, aromatic) 5.0 (s, 2H, $CH_2$ benzyl) 4.5 (s, 2H, $CH_2$ CBZ) 4.4 (m, 2H, 2×chiral) 2.6 (br app s, $CH_2$ Ser) 2.0 (br app s, CH Val) 0.9 (app d, 6H, $CH_3$).

EXAMPLE 20

Synthesis of 5-(N-benzyloxycarbonyl-(7—N-trityl)glutamyl-valyamino-1,3,4-thiadiazole-2-thione This compound was prepared according the method described in Example 11 using N-benzyloxycarbonyl-(N-trityl)glutamine in place of N-benzyloxycarbonyl-(O-benzyltyrosine).

An analytical sample was prepared by preparative TLC using $CH_2Cl_2$:MeOH (95:5), $R_f$=0.30. Melting point 146.8°–155.7° C. $^1$H-NMR ($d_6$-DMSO, int. std.) 14.1 (br s, NH thiadiazole) 12.6 (br s, NH amide thiadiazole) 8.5 (s, 1H, amide) 8.0 (s, 1H, amide) 7.2 (m 20H, aromatic) 5.0 (s, 2H, $CH_2$ CBZ) 4.4 (m, 1H, chiral) 4.1 (m, 1H, chiral) 2.4–1.6 (m, 5H) 0.8 (app s, 6H, $CH_3$).

EXAMPLE 21

Synthesis of 5-(N-benzyloxycarbonyl-((O-benzyl)tyrosyl)-amino-isobutyroylamino)-1,3,4-thiadiazole-2-thione The synthesis of methyl 2-aminoisobutyrate (AibOMe) was accomplished by esterifying 2-aminoisobutyric acid in methanolic HCl. The HCl salt was crystallized from methanol/ether. The remainder of the synthesis was carried out according to the procedure described in Example 11, using AibOMe in place of valine methyl ester hydrochloride.

An analytical sample was prepared by preparative TLC using $CH_2Cl_2$:MeOH (95:5), $R_f$=0.47. Melting point 106.5°–114.5° C. $^1$H-NMR ($d_6$-DMSO, int. std.) 14.0 (br s, NH thiadiazole) 11.8 (br s, NH amide thiadiazole) 8.4 (s, 1H, amide) 7.5–6.9 (m, 15H, aromatic+1 amide) 5.1 (s 2H, $CH_2$ benzyl) 4.9 (dd, 2H, $CH_2$ CBZ) 4.2 (m, 1H, chiral) 1.4 (s, 6H, $CH_3$).

EXAMPLE 22

Synthesis of 5-(N-benzyloxycarbonyl-((O-benzyl)tyrosyl)-phenylglycylamino)-1,3,4-thiadiazole-2-thione This compound was prepared according to the procedure described in Example 11 using phenylglycine methyl ester hydrochloride in place of valine methyl ester hydrochloride.

An analytical sample was prepared by preparative TLC using $CH_2Cl_2$:MeOH (95:5), $R_f$=0.42. Melting point 123.0°–127.8° C. $^1$H-NMR ($d_6$-DMSO, int. std.) 14.1–12.7 (br hump, NH and NH amide of thiadiazole) 9.0 (d, 1H, amide) 7.6–6.8 (m, 20H, aromatics+1 amide) 5.6 (d, 1H, chiral phenylglycyl) 5.1 (s 2H, $CH_2$ benzyl) 4.9 (s, 2H, $CH_2$ CBZ) 4.4 (br app s, 1H, chiral Tyr) 3.0–2.6 (m, 2H, $CH_2$ Tyr).

EXAMPLE 23

Synthesis of 5-(N-benzyloxycarbonyl((O-methylene-2-naphthyl)tyrosyl)-valylamino)-1,3,4-thiadiazole-2-thione The synthesis of O-methylene-2-naphthyl-tyrosine was accomplished using standard procedures through the copper chelate (Bodanszky and Bodanszky "The Practice of Peptide Synthesis") and crystallized from aqueous acetic acid. Acylation of O-methylene-2-naphthyl-tyrosine was accomplished using Schotten-Baumann conditions (Bodanszky, "Principles of Peptide Synthesis") in a water dioxane mixture with Cbz-Cl. 5N NaOH was used to maintain the pH at about 10. After the reaction was complete, the mixture was adjusted to pH 7, concentrated to half-volume, diluted with water, acidified to pH 3 and extracted with ethyl acetate. The combined organic washes were dried ($Na_2SO_4$) and evaporated to dryness. The crude product, N-benzyloxycarbonyl-(O-methylene-2-naphthyl)tyrosine (Cbz-Tyr(Naph)), was used without further purification.

The remainder of the synthesis was carried out according to the procedure described in Example 11, using Cbz-Tyr (Naph) in place of N-benzyloxycarbonyl-(0-benzyl) tyrosine.

An analytical sample was prepared by preparative TLC using $CH_2Cl_2$:MeOH (95:5), $R_f$0.45. Melting point 104.8°–111.4° C. $^1$H-NMR ($d_6$-DMSO, int. std.) 14.1 (s, 1H, NH thiadiazole) 12.6 (s, 1H, NH amide thiadiazole) 8.2 (d, 1H, amide) 8.0–6.9 (m, 17H, aromatics+1 amide) 5.2 (s, 2H, $CH_2$ benzylic) 4.9 (s, 2H, $CH_2$ CBZ) 4.3 (m, 2H, 2×chiral) 0.9 (m, 6H, $CH_3$).

EXAMPLE 24

Synthesis of 5-(N-benzyloxycarbonyl-((γ-N-trityl)glutamyl)-phenylglycylamino)-1,3,4-thiadiazole-2-thione This compound was prepared according to the procedure described in Example 11 using N-benzyloxycarbonyl-((γ-N-trityl) glutamine and phenylglycine methyl ester hydrochloride in place of N-benzyloxycarbonyl-(O-benzyl)tyrosine) and valine methyl ester hydrochloride.

An analytical sample was prepared by preparative TLC using $CH_2Cl_2$:MeOH (95:5), $R_f$0.46. Melting point 158.4°–167.4° C. $^1$H-NMR ($d_6$-DMSO, int. std.) 14.0–12.6 (br hump, 1.5H, NH and NH amide thiadiazole) 8.7 (d, 1H, amide) 8.5 (s, 1H, amide) 7.6–6.9 (m, 25H, aromatics) 5.6 (app dd, 1H, chiral phenylglycyl) 5.0 (s, 2H, $CH_2$ CBZ) 4.1 (m, 1H, chiral Gln) 2.4–1.6 (m, 4H).

EXAMPLE 25

Synthesis of 5-(N-benzyloxycarbonyl-(γ-N,N-dibenzyl)glutamyl-phenylglycylamino)-1,3,4-thiadiazole2-thione Dicyclohexylcarbodiimide (0.22 grams), then N-benzyloxycarbonyl-(γ-N,N-dibenzyl)glutamine-phenylglycine (0.48 grams) and the 1-hydroxybenzotriazole (0.15 grams) were dissolved in 5 mL of anhydrous DMF. The solution was kept in room temperature until dicyclohexylurea precipitation was completed (about 40 minutes). 5-Amino-1,3,4-thiadiazole-2-thione (0.39 grams) was added and solution was left for 2 days. An excess of ethyl acetate was added (50mL) and dicyclohexylurea was filtered off. The supernatant was washed several times washed with 10% aqueous citric acid (3×20 mL), 5% aqueous sodium bicarbonate (3×20 mL) and brine (3×20 mL). The ethyl acetate layer was dried with sodium sulfate and evaporated to dryness. The light yellow solid was purified by preparative TLC. The resulting as white solid was dried at 50° C. under vacuum. M.P. 140° C. $R_f$0.37; eluent: methanol: methylene-chloride 5:95. NMR spectrum ($d_6$-DMSO) 14.1 (s, 1H), 12.8 (s, 1H), 8.8 (s, 1H), 7.3 (m, 21H), 5.6 (d, 1H), 5.0 (d, 2H), 4.4 (m, 4H), 4.2 (m, 1H), 2.5 (m, 2H), 2.0 (m, 2H).

EXAMPLE 26

Synthesis of 5-(N-benzyloxycarbonyl-(γ-N-2-phenylethyl)glutamyl phenylglycylamino)-1,3,4-thiadiazole-2-thione This compound was prepared according to the procedure described in Example 25 using N-benzyloxycarbonyl-((γ-N-phenylethyl)glutamine-phenylglycine in place of N-benzyloxycarbonyl-((γN,N-dibenzyl)glutamine-phenylglycine. M.P. 145° C. $R_f$0.40; eluent: methanol: methylene-chloride 10:100. NMR spectrum ($d_6$-DMSO) 14.1 (s, 1H), 12.8 (s, 1H), 8.8 (s, 1H), 7.9 (m, 1H), 7.2 (m, 16H), 5.7 (d, 2H), 4.1 (m, 1H), 3.2 (m, 2H), 2.6 (m, 2H), 2.5 (m 2H), 2.0 (m, 2H).

EXAMPLE 27

Synthesis of 5-(N-benzyloxycarbonyl-leucyl-valylamino)-1,3,4-thiadiazole-2-thione N-Benzyloxycarbonyl-luecyl-valine (0.419 grams), 1-hydroxybenzotriazole (0.186 grams) and 5-amino-1,3,4-thiadiazole-2-thione (0.497 grams) were added to 6 mL of anhydrous DMF, followed by dicyclohexylcarbodiimide (0.277 grams). The reaction mixture was allowed to stir for three days at room temperature. The DMF was partially removed on a rotary evaporator and the residue was diluted with 100 mL of ethyl acetate. The dicyclohexylurea was filtered off and the filtrate was extracted with 10% citric acid (3×30 mL), 10% sodium bicarbonate (3×30 mL), and brine solution (3×30 mL). The ethyl acetate solution was dried over sodium sulfate, filtered and evaporated to dryness on a rotary evaporator. The final product was purified from preparative TLC and gave one spot material on TLC (Rf 0.67: eluent; methylene chloride: methanol 95:5). M.P. 146° C. NMR spectrum ($d_6$-DMSO) 14.1 (s, 1H), 12.70 (s, 1H), 8.1 (s, 1H), 7.4 (s, 6H), 5.0 (s, 2H), 4.3 (s, 1H), 4.1 (s, 1H), 1.8 (m, 1H), 1.4 (m, 2H), 0.90 (s, 12H).

EXAMPLE 28

Synthesis of 5-(N-Benzyloxycarbonyl-isoleucyl-valylamino)-1,3,4-thiadiazole-2-thione This compound was prepared by the procedure described in Example 28 except that (benzyloxycarbonyl)isoleucyl-valine was used in place of N-(benzyloxycarbonyl)leucyl-valine. The final product was purified by preparative TLC and gave one spot by TLC analysis (Rf 0.55: eluent; Methylene chloride: methanol 95:5). M.P.197°–198° C. NMR spectrum ($d_6$-DMSO) 14.1 (s, 1H), 12.70 (s, 1H), 8.1 (s, 1H), 7.7(s, 1H), 7.3 (s, 6H), 5.0 (s, 2H), 4.1 (s, 1H), 1.8 (m, 2H), 1.4 (m, 1H), 1.2 (m, 3H), 0.80 (s, 9H).

EXAMPLE 29

Synthesis of Synthesis of 5-(N-Benzyloxycarbonyl-(2-flouro)phenyl-valylamino)-1,3,4-thiadiazole-2-thione This compound was prepared by the procedure described in Example 27 except that N-(benzyloxycarbonyl)-(2-fluoro)phenylalanyl-valine was used in place of N-(benzyloxycarbonyl)leucyl-valine. The final product was purified from preparative TLC and gave one spot by TLC analysis (Rf 0.81: eluent; Methylene chloride: methanol 95:5). M.P.148° C. NMR spectrum ($d_6$-DMSO) 14.1 (s, 1H), 12.70 (s, 1H), 7.9 (s, 1H), 7.3 (m, 10H), 5.0 (s, 2H), 4.5 (s, 1H).

EXAMPLE 30

Synthesis of Synthesis of 5-(N-benzyloxycarbonyl-(O-Benzyl)tyrosyl-glycylamino)-1,3,4-thiadiazole-2-thione This compound was prepared by the procedure described in Example 27 except that N-(benzyloxycarbonyl)-(O-benzyl)tyrosyl-glycine was used in place of N-(benzyloxycarbonyl)leucyl-valine and the reaction was stirred for six days. The final product was purified from preparative TLC and gave one spot by TLC analysis (Rf 0.65: eluent; Methylene chloride: methanol 95:5). M.P.201°–202° C. NMR spectrum ($d_6$-DMSO) 14.1 (s, 1H), 12.5 (s, 1H), 8.5 (s, 1H), 7.9–6.6 (m, 14H), 5.1 (s, 2H), 4.9 (s, 2H), 4.2 (s, 1H), 4.0 (s, 2H).

EXAMPLE 31

Synthesis of Synthesis of 5-(N-benzyloxycarbonyl-(O-Benzyl)tyrosyl-(t-butyl)glycylamino)-1,3,4-thiadiazole-2-thione This compound was prepared by the procedure described in Example 27 except that N-(benzyloxycarbonyl)-(O-benzyl)tyrosyl-(t-butyl)glycine was used in place of N-(benzyloxycarbonyl)leucyl-valine and the reaction was stirred for six days. The final product was purified from preparative TLC and gave one spot by TLC analysis (Rf 0.84: eluent; Methylene chloride: methanol 95:5). M.P.146° C. NMR spectrum ($d_6$-DMSO) 14.05 (s, 1H), 12.3 (s, 1H) 7.6–6.9 (m, 14H), 5.6 (s, 1H), 5.1 (s, 2H), 4.9 (s, 2H), 4.4 (m, 2H), 1.0 (m, 14H).

EXAMPLE 32

Synthesis of Synthesis of 5-(N-benzyloxycarbonyl-(O-Benzyl)tyrosyl-(t-butyl)glycylamino)-1,3,4-thiadiazole-2-thione This compound was preparedly the procedure described in Example 27 except that N-(benzyloxycarbonyl)-(O-benzyl)tyrosyl-(cyclohexyl)glycine was used in place of N-(benzyloxycarbonyl)leucyl-valine and the reaction was stirred for four days. The final product was purified from preparative TLC and gave one spot by TLC analysis (Rf 0.64: eluent; Methylene chloride: methanol 95:5). M.P.150° C. NMR spectrum ($d_6$-DMSO) 14.1 (s, 1H), 12.6 (s, 1H), 7.7–6.8 (m, 14H), 5.0 (s, 2H), 4.9 (s, 2H), 4.3 (broad s, 2H), 1.6 (m, 6H), 1.1 (m, 6H).

EXAMPLE 33

Synthesis of 5(N-benzyloxycarbonyl-(N',N'-dibenzylamino)phenylalanine-phepylglycylamino)-1,3,4-thiadiazole-2-thione N-Benzyloxycarbonyl-(p-N,N-dibenzylamino) phenylalanine (0.294 grams), 1-hydroxybenzotriazole (0.89 grams), and 5-phenylalanyl)amino-1,3,4-thiadiazole-2-thione hydrochloride (0.193 grams) were added to 5 mL methylene chloride, followed by dicyclohexylcarbodiimide (0.132 grams). The reaction mixture was allowed to stir for 24 hours. The methylene chloride was partially removed on the rotary evaporator and the residue was diluted with 100 mL of ethyl acetate. The dicyclohexylurea was filtered off and the filtrate was extracted with 10% citric acid (3×20 mL), 10% sodium carbonate (3×20 mL), and brine solution (3×20 mL). The ethyl acetate was dried over sodium sulfate and evaporated to dryness on the rotary evaporator. The final product was purified by preparative TLC and gave one spot by TLC (Rf 0.80: eluent; Methylene chloride: methanol 95:5). M.P. 197°–199° C. NMR spectrum ($d_6$-DMSO) 14.1 (s, 1H), 12.9 (s, 1H), 8.9 (d, 1H), 7.7–6.6 (m, 24H), 5.8 (d, 1H), 4.9 (dd, 2H), 4.6 (s, 4H), 4.2 (s 1H).

EXAMPLE 34

Synthesis of 5-(N-benzyloxycarbonyl-phenylalanyl-tryptonyl-valylamino)-1,3,4-thiadiazole-2-thione Dicyclohexylcarbodiimide (0.47 grams) was dissolved in 5 mL of anhydrous DMF, followed by N-(benzyloxycarbonyl)phenyalanyl-tryptonyl-valine (1.34 grams) and 1-hydroxybenzotriazole (0.45 grams). The solution was kept at room temperature until dicyclohexylurea was completely precipitated (about 1 hour). 5-Amino-1,3,4-thiadiazole-2-thione (1.1 grams) was added and the mixture was allowed to stir for 2 days. An excess of ethyl acetate was added (150 mL) and the organic layer was washed with 5% aqueous sodium bicarbonate (3×50 mL), 10% aqueous citric acid (3×50 mL) and water (3×50 mL). The organic layer was separated, dried over sodium sulfate and evaporated to dryness. The residue was recrystallized from ethyl acetate/pentane to give a white solid. M.P. 203°–206° C. NMR spectrum ($d_6$-DMSO) 14.1 (s, 1H), 12.6 (s, 1H), 10.8 (s, 1H), 8.25 (d, 1H), 8.15 (d, 1H), 7.6–6.8 (m, 16 H, NH+aromatics), 4.9 (s, 2H), 4.65 (m, 1H), 4.35 (m, 1H), 4.25 (m, 1H), 3.2–2.6 (m, 4H), 2.0 (m, 1H), 0.9 (bs, 4H).

EXAMPLE 35

Synthesis of S-(N-Benzyloxycarbonyl-glycyl-tyrosyl-((O-benzyl) tyrosyl)-phenylglycyl amino)-1,3,4-thiadiazole-2-thione
Synthesis of N-t-Butoxycarbonyl-(O-benzyl)tyrosyl-phenylglycyl-methylester Phenylglycine methyl ester hydrochloride (1.8 grams), triethylamine (1.3 mL) and HBT (1.09 grams) were dissolved in 30 mL $CH_2Cl_2$. N-t-Boc-(O-benzyl)tyrosine (3.0 grams) was then added and the solution was stirred at room temperature for 15 minutes. Dicyclohexylcarbodiimide (1.83 grams) was then added and the solution stirred for 6 hours. An excess of methylene chloride (250 mL) was added and the resulting solution was washed until TLC analysis showed one spot. (Rf 0.71: eluent; methanol:chloroform 5:95). The organic layer was separated, dried over sodium sulfate and evaporated to dryness. The product was obtained as an off whitepowder. M.P.130–132. NMR spectrum (d6-DMSO) 8.6 (d, 1H), 6.7–7.6 (m, 16H, NH+aromatics), 5.5 (m, 1H), 5 (s, 2H), 4.3 (m, 1H), 3.7 (s, 3H) 2.9 (m, 2H), 1.3 (s, 9H).

Synthesis of N-t-Butoxycarbonyl-(O-benzyl)tyrosyl-phenylglycine

2N NaOH was dissolved in 10 mL of dioxane, followed by the addition of N-t-boc-(O-benzyl)tyrosyl-phenylglycine methyl ester. The solution was stirred at room temperature for 45 minutes. An excess of water (60 mL) was added to the reaction mixture and the resulting solution was washed with ethyl acetate (2×30 mL). The aqueous layer was separated and acidified to pH 3. The resulting solution was extracted with ethyl acetate (5×50 mL), dried over sodium sulfate and evaporated to dryness. The product was obtained as an off white powder. M.P.158–161. NMR spectrum (d6-DMSO) 8.6 (d, 1H), 6.7–7.5 (m, 16H, NH+aromatics), 5.3 (m, 1H), 5 (s, 2H), 4.2 (m, 1H), 2.9 (m, 2H), 1.3 (s, 9H).

Synthesis of 5-(N-t-Butoxycarbonyl-(O-benzyl)tyrosyl-phenylglycineamino)-1,3,4-thiadiazole-2-thione 5-Amino-1,3,4-thiadiazole-2-thione (0.875 grams) was dissolved under a nitrogen atmosphere in 8 mL of anhydrous DMF. N-t-Boc-(O-benzyl)tyrosyl-phenylglycine (1.0 grams) and HBT (0.33 grams) were then added and the solution was stirred at room temperature for about 30 minutes. Dicyclohexylcarbodiimide (0.5 grams) was then added and the reaction was stirred for 3 days. An excess of ethyl acetate was added (100 mL) and the resulting solution was washed several times with 5% aqueous sodium bicarbonate, 10% aqueous citric acid and water until TLC analysis showed one spot (Rf 0.45: eluent; methanol: chloroform 5:95). The organic layer was separated, dried over sodium sulfate and evaporated to dryness. The product was obtained as a yellow residue which was recrystalised from methylene chloride-petroleum. M.P. 118–120.5 NMR spectrum (d6-DMSO) 14.1 (s, 1H), 12.9 (s, 1H), 8.8 (d, 1H), 6.8–7.8 (m, 19H, NH+aromatics), 5.6 (m, 1H), 5.0 (d, 4H), 4.3 (m, 1H), 2.9 (m, 2H), 1.3 (s, 9H).

Synthesis of 5-(O-Benzyl)tyrosyl-phenylglycylamino-1,3,4-thiadiazole-2-thione hydrochloride 4N HCl (5 mL) followed by 5-(N-t-butoxycarbonyl-(O-benzyl)tyrosyl-phenylglycylamino)-1,3,4-thiadiazole-2-thione (1.0 grams) were dissolved in 5 mL of dioxane. Nitrogen was bubbled through the reaction mixture for 15 minutes and the reaction was then allowed to stir at room temperature overnight. The reaction mixture was evaporated to dryness to give a yellow powder as the product. NMR spectrum (d6-DMSO) 14.1 (s, 1H), 12.9 (s, 1H), 8.8 (d, 1H), 6.8–7.8 (m, 19H, NH+aromatics), 5.6 (m, 1H), 5.0 (d, 4H), 4.3 (m, 1H), 2.9 (m, 2H).

Synthesis of 5-(N-benzyloxycarbonyl-glycyl-tyrosyl-(O-benzyl)tyrosyl)-phenylglycylamino)-1,3,4-thiadiazole-2-thione 5-((O-benzyl)tyrosyl-phenylglycylamino)-1,3,4-thiadiazole-2-thione hydrocholoride (135 mg), triethylamine (35 µl) and HBT (33 mg) were dissolved in 2 mL ethyl acetate, followed by the addition of N-(t-boc-glycyl-tyrosine) (100 mg). The solution was stirred at room temperature for 15 minutes. Dicyclohexylcarbodiimide (55 mg) was added to the reaction mixture, which was then stirred for 24 hours. An excess of ethyl acetate (50 mL) was added and the resulting solution was washed several times with 5% aqueous sodium bicarbonate, 10% aqueous citric acid and brine until TLC analysis showed one spot. (Rf:0.4, eluent; methanol:chloroform 5:95). The organic layer was separated, dried over sodium sulfate and evaporated to dryness. The product was recrystallized from methylene chloride-petroleum to give an off white powder. M.P.

143–154. NMR spectrum (d6-DMSO) 14.1(s, 1H), 12.9 (s, 1H), 8.8 (m, 1H), 8.1 (m, 1H), 7.8 (m, 1H), 6.6–7.6 (m, 25H, NH+aromatics), 5.5 (m, 1H), 5.0 (s, 4H), 4.3–4.7 (m, 2H), 3.7 (s, 2H ), 2.8 (m, 4H).

EXAMPLE 36

Synthesis of 5-(N-benzyloxycarbonyl-prolyl-phenylalanyl-((O-benzyl)tyrosyl)-phenylglycylamino)-1,3,4-thiadiazole-2-thione 5-((O-Benzyl)tyrosyl-phenylglycylamino)-1,3,4-thiadiazole-2-thionone (159.4 mg), triethylamine (42 µl) and HBT (38 mg) were dissolved in 2 ml ethyl acetate, followed by the addition of N-boc-prolyl-phenylalanine (125 mg), triethylamine (42 µL) and HBT (38 mg). The solution was stirred at room temperature for 15 minutes. Dicyclohexylcarbodiimide (65 mg) was then added and the reaction stirred for 24 hours. An excess of ethyl acetate (50 mL) was added and the resulting solution was washed several times with 5% aqueous sodium bicarbonate, 10% aqueous citric acid and brine until TLC analysis showed one spot. (Rf: 0.38, eluent; methanol:chloroform 5:95). The organic layer was separated, dried over sodium sulfate and evaporated to dryness. The product was recrystallized from methylene chloride-petroleum to give an off white powder. M.P. 144.7–149.2. NMR spectrum (d6-DMSO) 14.05 (s, 1H), 12.8 (s, 1H), 9 (m, 1H), 8 (m, 2H) 6.8–7.6 (m, 24H, aromatics), 5.5 (m, 1H), 5.0 (m, 4H), 4.8 (m, 1H), 4.5 (m, 1H), 4.1 (m, 1H ), 2.6–3.0 (m, 4H), 1.4–1.8 (m, 6H).

EXAMPLE 37

Assay of Stromelysin Inhibition Activity

Stromelysin was first activated with trypsin. This was done by preparing a reaction mixture in H-150 (H-150 consists of 10 mM $CaCl_2$, 150 mM NaCl and 100 mM HEPES at pH 7.4) containing a final concentration of 25 µg/mL trypsin and 2.2 µM of stromelysin (Marcy et al., *Biochemistry*, 30:6476 (1991); Koklitis et al., *Biochem. J.*, 376:217 (1991). The reaction was incubated for 30 minutes at 37° C. and then quenched by adding trypsin inhibitor agarose to the reaction mixture at a 20 fold excess with respect to trypsin.

The reaction mixture was centrifuged at 14,000 rpm (16,000 ×g) for 30 minutes using an Eppendorf Centrifuge 5415C. The supernant, which contains activated stromelysin, was concentrated with a Centricon 10 (5000 g, 1 hour). A sample was analyzed by Bradford total protein assay and 12% SDS polyacrylamide gel electrophoresis.

All steps of the stromelysin inhibition assay were performed at room temperature. Assay solutions were prepared for each inhibitor tested. Activated stromelysin was added to a stirred covelte to a final concentration of 2 nM in 2 mL of H-150 buffer. 4 µL 5 mM coumarin peptide substrate was dissolved in DMSO and the initial rate of hydrolysis was measured for 100–200 seconds.

Substrate hydrolysis was assessed by fluorescence using a slit width of 10:10, excitation at 328 nm and emission at 393 nm. Ki was calculated based on the assumption of simple competitive inhibition and a substrate concentration much less than Km. The results of these assays are listed in Table I as the $IC_{50}$. 2 µL of 10 mM inhibitor in DMSO was added and the reduction in hydrolysis rate measured. The addition of 2 µL of inhibitor was continued until a 30–70% inhibition was observed.

TABLE I

STROMELYSIN INHIBITION DATA

| Compounds | $K_{i(app)}$ [nM] |
|---|---|
| 5-(N-benzyloxycarbonyl-tryptonylamino)-1,3,4-thiadiazole-2-thione | 3370 |
| 5-(N-(9-fluorenylmethoxycarbonyl)valylamino)1,3,4-thiadiazole-2-thione | 128 |
| 5-(N-benzyloxycarbonyl-phenylalanylamino)-1,3,4-thiadiazole-2-thione | 2360 |
| 5-(N-(9-fluorenylmethoxycarbonyl-norvalyl)-1,3,4-thiadiazole-2-thione | 509 |
| 5-(N-(9-fluorenylmethoxycarbonyl)tryptonylamino)-1,3,4-thiadiazole-2-thione | 341 |
| 5-(N-(9-fluorenylmethoxycarbonyl)leucylamino)-1,3,4-thiadiazole-2-thione | 184 |
| 5-(N-(9-fluorenlylmethoxycarbonyl)methionylamino-1,3,4-thiadiazole-2-thione | 195 |
| 5-(N-(9-fluorenylmethoxycarbonyl)homophenylalanylamino)-1,3,4-thiadiazole-2-thione | 436 |
| 5-(N-t-butoxycarbonyl-leucylamino)-1,3,4-thiadiazole-2-thione | 10200 |
| 5-(N-t-butoxycarbonyl-homophenylalanylamino)-1,3,4-thiadiazole-2-thione | 11900 |
| 5-(N-((4-phenyl)phenylacetyl)valylamino)-1,3,4-thiadiazole-2-thione | 100 |
| 5-(N-benzyloxycarbonyl-(ortho-fluoro)phenylalanylamino)-1,3,4-thiadiazole-2-thione | 630 |
| 5-(N-(8-quinolinesulfonyl)phenylalanyl-valylamino-1,3,4-thiadiazole-2-thione | 531 |
| 5-(N-(2-methylthionicotyl)phenylalanyl-valyamino)-1,3,4-thiadiazole-2-thione | 917 |
| 5-(N-hydrocinamoyl-phenylalanyl-valylamino-1,3,4-thiadiazole-2-thione | 267 |
| 5-(N-(4-phenylbenzoyl)phenylalanyl-valylamino)-1,3,4-thiadiazole-2-thione | 82 |
| 5-(N-nonanoyl-phenylalanyl-valylamino)-1,3,4-thiadiazole-2-thione | 83 |
| 5-(N-(4-phenyl)phenylacetyl-phenylalanyl-valylamino)-1,3,4-thiadiazole-2-thione | 135 |
| 5-(N-(4-benzyloxy)benzoyl-phenylalanyl-valylamino)-1,3,4-thiadiazole-2-thione | 61 |
| 5-(N-(4-phenoxy)benzoyl-phenylalanyl-valyamino)-1,3,4-thiadiazole-2-thione | 101 |
| 5-(N-acetyl-leucyl-leucylamino)-1,3,4-thiadiazole-2-thione | 6440 |
| 5-(N-(4-(4-t-butylphenylsulfonamino)benzoyl)-phenylalanyl-valylamino)-1,3,4-thiadiazole-2-thione | 44 |
| 5-(N-benzyloxycarbonyl-phenylalanyl-leucylamino-1,3,4-thiadiazole-2-thione | 169 |
| 5-(N-benzyloxycarbonyl-leucyl-tyrosylamino-1,3,4-thiadiazole-2-thione | 1300 |
| 5-(N-benzyloxycarbonyl-phenylalanyl-alanylamino)-1,3,4-thiadiazole-2-thione | 1400 |
| 5-(N-benzyloxycarbonyl-phenylalanyl-glycylamino)-1,3,4-thiadiazole-2-thione | 3950 |
| 5-(N-benzyloxycarbonyl-phenylalanyl-methionylamino)-1,3,4-thiadiazole-2-thione | 1121 |
| 5-(N-benzyloxycarbonyl-phenylalanyl-valylamino)-1,3,4-thiadiazole-2-thione | 279 |
| 5-(N-benzyloxycarbonyl-tryptoyl-valylamino)-1,3,4-thiadiazole-2-thione | 741 |

TABLE I-continued

STROMELYSIN INHIBITION DATA

| Compounds | $K_{i(app)}$ [nM] |
|---|---|
| 5-(N-benzyloxycarbonyl-tryptoyl-phenylalanylamino)-1,3,4-thiadiazole-2-thione | 225 |
| 5-(N-benzyloxycarbonyl-leucyl-methionylamino)-1,3,4-thiadiazole-2-thione | 490 |
| 5-(N-benzyloxycarbonyl-(2-(1-naphtyl))alanyl-valylamino-1,3,4-thiadiazole-2-thione | 190 |
| 5-(N-benzyloxycarbonyl-(2-(2-naphtyl))alanyl-valylamino-1,3,4-thiadiazole-2-thione | 221 |
| 5-(N-benzyloxycarbonyl-(O-benzyl)tyrosyl-valylamino-1,3,4-thiadiazole-2-thione | 80 |
| 5-(N-benzyloxycarbonyl-(para-F)phenylalanyl-valylamino)-1,3,4-thiadiazole-2-thione | 156 |
| 5-(N-benzyloxycarbonyl-leucyl-valylamino)-1,3,4-thiadiazole-2-thione | 660 |
| 5-(N-benzyloxycarbonyl-cyclohexylglycyl-valylamino)-1,3,4-thiadiazole-2-thione | 180 |
| 5-(N-benzyloxycarbonyl-isoleucyl-valylamino)-1,3,4-thiadiazole-2-thione | 940 |
| 5-(N-benzyloxycarbonyl-(O-benzyl)glutamoyl-valylamino)-1,3,4-thiadiazole-2-thione | 146 |
| 5-(N-benzyloxycarbonyl-(p-nitro)phenylalanyl-valylamino-1,3,4-thiadiazole-2-thione | 180 |
| 5-(N-benzyloxycarbonyl-((p-benzyloxycaronylamino)phenylalanyl)-valylamino)-1,3,4-thiadiazole-2-thione | 62 |
| 5-(N-benzyloxycarbonyl-((3,4-diiodo)phenylalanyl)-valylamino)-1,3,4-thiadiazole-2-thione | 97 |
| 5-(N-benzyloxycarbonyl-((S-benzyl)cysteinyl)-valylamino)-1,3,4-thiadiazole-2-thione | 202 |
| 5-(N-benzyloxycarbonyl-((ortho-flouro)phenylalanyl)-valylamino)-1,3,4-thiadiazole-2-thione | 633 |
| 5-(N-benzyloxycarbonyl-(O-benzyl)seryl)-valylamino)-1,3,4-thiadiazole-2-thione | 236 |
| 5-(N-benzyloxycarbonyl-((N-trityl)glutamyl)-valylamino)-1,3,4-thiadiazole-2-thione | 91 |
| 5-(N-benzyloxycarbonyl-((O-benzyl)tyrosyl)-aminoisobutyroylamino)-1,3,4-thiadiazole-2-thione | 237 |
| 5-(N-benzyloxycarbonyl-((O-benzyl)tyrosyl)-phenylglycylamino)-1,3,4-thiadiazole-2-thione | 39 |
| 5-(N-benzyloxycarbonyl-((O-methylene-2-naphtyl)tyrosyl)-valylamino)-1,3,4-thiadiazole-2-thione | 62 |
| 5-(N-benzyloxycarbonyl-((O-benzyl)tyrosyl-(t-butyl)glycylamino)-1,3,4-thiadiazole-2-thione | 89 |
| 5-(N-benzyloxycarbonyl-((N-trityl)glutamyl)-phenylglycylamino)-1,3,4-thiadiazole-2-thione | 50 |
| 5-(N-benzyloxycarbonyl-((O-benzyl)tyrosyl)-cyclohexylglycylamino)-1,3,4-thiadiazole-2-thione | 71 |
| 5-(N-benzyloxycarbonyl-((O-benzyl)tyrosyl)-phenylglycylamino)-1,3,4-thiadiazole-2-thione | 64 |
| 5-(N-benzyloxycarbonyl-((N,N-dibenzyl)glutamyl)-phenylglycylamino)-1,3,4-thiadiazole-2-thione | 19 |
| 5-(N-benzyloxycarbonyl-((p-N,N-dibenzylamino)phenylalanyl)-phenylglycylamino)-1,3,4-thiadiazole-2-thione | 205 |
| 5-(N-benzyloxycarbonyl-((O-benzyl)tyrosyl)-leucylamino)-1,3,4-thiadiazole-2-thione | 96 |
| 5-(N-benzyloxycarbonyl-(N-2-phenylethyl)glutamyl-phenylglycylamino)-1,3,4-thiadiazole-2-thione | 57 |
| 5-(N-benzyloxycarbonyl-phenylalanyl-leucyl-tryptonylaimino)-1,3,4-thiadiazole-2-thione | 246 |
| 5-(N-benzyloxycarbonyl-phenylalanyl-valyl-tryptonylamino)-1,3,4-thiadiazole-2-thione | 273 |
| 5-(N-benzyloxycarbonyl-prolyl-leucyl-alanylamino)-1,3,4-thiadiazole-2-thione | 1740 |
| 5-(N-benzyloxycarbonyl-phenylalanyl-tryptonyl-valylamino)-1,3,4-thiadiazole-2-thione | 60 |
| 5-(N-benzyloxycarbonyl-lysyl(N-ε-t-butyloxycarbonyl)-tyrosyl(O-benzyl)-phenylglycylamino-1,3,4-thiadiazole-2-thione | 148 |
| 5-(N-benzyloxycarbonyl-lysyl-((O-benzyl)tyrosyl)-phenylglycylamino)-1,3,4-thiadiazole-2-thione | 1890 |
| 5-(N-benzyloxycarbonyl-glycyl-tyrosyl-((O-benzyl)tyrosyl)-phenylglycylamino)-1,3,4-thiadiazole-2-thione | 110 |

EXAMPLE 38

Assay of Human Neutrophil Collagenase Inhibition Activity

H-150 buffer, pH 7.4, was prepared by adding $CaCl_2H_2O$ (1.47 grams), NaCl (8.77 grams) and N-[2-hydroxyethyl] piperazine-N'-[2-ethanesulfonic acid] (23.83 grams) to distilled and deionized water and then bringing the final volume of the solution to 1 liter.

A reaction mixture with a final volume of 2.0 mL was prepared from H-150 buffer, human neutrophil collagenase (Schnierer, et al., *Blochem. Biophys. Res. Comm.*, 191:319 (1993); Knight et al., *Federation of Europena Biochemical Societies* 296:263 (1992)) (2 nM). Coumarin peptide substrate (4 μL of a 5 mM solution in dimethyl sulfoxide) was added to the reaction mixture. The rate of hydrolysis was determined for about 100–200 seconds by measuring the fluorescence of the reaction at ex328 nanometers and em329 nanometers using a Hitachi F-2000 Fluorescence Spectrophotometer.

2 μL of a 10 mM inhibitor stock solution (in dimethyl sulfoxide) is added and the reduction in the rate of hydrolysis is determined. Additional 2 μL aliquots of the stock inhibitor solution is added until a 30% to 70% inhibition is observed. $K_i$ is calculated on the assumption of simple competitive inhibition and that the substrate concentration is much less than $K_m$. The results are shown in Table II.

TABLE II

INHIBITION DATA FOR HUMAN NEUTROPHIL COLLAGENASE

| Compounds | $K_{i(app)}$ [nM] |
|---|---|
| 5-(N-t-butyloxycarbonyl-((O-benzyl)tyrosyl-phenylglycylamino)-1,3,4-thiadiazole-2-thione | 0.99 |
| 5-(N-(4-(4-t-butylphenylsulfonylamino)benzoyl)phenylalanyl-valylamino)-1,3,4-thiadiazole-2-thione | 1.04 |
| 5-(N-benzyloxycarbonyl-((p-benzyloxycarbonylamino)phenylalanyl)-valylamino)-1,3,4-thiadiazole-2-thione | 1.17 |
| 5-(N-benzyloxycarbonyl-phenylalanyl-leucyl-tryptonylamino)-1,3,4-thiadiazole-2-thione | 1.45 |
| 5-(N-benzyloxycarbonyl-((O-benzyl)tyrosyl)phenylglycylamino)-1,3,4-thiadiazole-2-thione | 1.57 |
| 5-(N-(4-phenoxy)benzoyl-phenylalanyl-valylamino)-1,3,4-thiadiazole-2-thione | 1.67 |
| 5-(N-(4-phenylbenzoyl)phenylalanyl-valylamino)-1,3,4-thiadiazole-2-thione | 2.6 |
| 5-(N-benzyloxycarbonyl-phenylalanyl-valylamino)-1,3,4-thiadiazole-2-thione | 4.8 |
| 5-(N-benzyloxycarbonyl-(O-benzyl)tyrosyl-valylamino-1,3,4-thiadiazole-2-thione | 2.15 |
| 5-(N-benzyloxycarbonyl-(O-benzyl)tyrosyl-leucylamino)-1,3,4-thiadiazole-2-thione | 1.83 |

TABLE II-continued

INHIBITION DATA FOR HUMAN NEUTROPHIL COLLAGENASE

| Compounds | $K_{i(app)}$ [nM] |
|---|---|
| 5-(N-benzyloxycarbonyl-(S-benzyl)cysteinyl-valylamino)-1,3,4-thiadiazole-2-thione | 3.2 |
| 5-(N-benzyloxycarbonyl-phenylalanyl-valylamino)-1,3,4-thiadiazole-2-thione | 7.8 |
| 5-(N-benzyloxycarbonyl-phenylalanyl-methionylamino)-1,3,4-thiadiazole-2-thione | 7.8 |
| 5-(N-benzyloxycarbonyl-((γ-N-2-phenylethyl)glutamyl)-phenylglycylamino)-1,3,4-thiadiazole-2-thione | 0.54 |
| 5-(N-benzyloxycarbonyl-phenylalanyl-tryptoyl-valylamino)-1,3,4-thiadiazole-2-thione | 2.4 |
| 5-(N-benzyloxycarbonyl-phenylalanyl-homophenylalanylamino)-1,3,4-thiadiazole-2-thione | 2.9 |

EXAMPLE 39

Assay of 72 KD Gelatinase Inhibition Activity

H-150 buffer, pH 7.4, was prepared by $CaCl_2H_2O$ (1.47 grams), NaCl (8.77 grams) and N-[2-hydroxyethyl]piperazine-N'-[2-ethanesulfonic acid](23.83 grams) to distilled and deionized water and then bring the final volume of the solution to 1 liter. An reaction mixture having a final volume of 250 μL was prepared with H-150 buffer, 40 μgrams of Pro-72KD gelatinase (Strongin, et al., *J. Biol. Chem.* 268:14033 (1993); Goldberg, et al., *J. Biol. Chem.*, 267:4583 (1992); Kleiner, et al., *Biochemistry* 32:1583 (1993)) and p-aminophenyl mercuric acetate (Sigma Chemical Co., St. Louis, Mo.) (1 mM). The reaction mixture was then incubated for 3 hours at 25° C.

The reaction mixture was applied to a NAP-5 column (G-25 SEPHADEX™, Pharmacia). Fractions containing 92KD gelatinase were identified using 12% SDS polyacrylamide gel electrphoresis and concentrated to about 100–200 μliters by centrifigation (5000 g, 15 minutes).

A solution containing H-150 buffer (2.0 mL), 72KD gelatinase (180 pM) and ethylphenolpoly(ethyleneglycolether)$_n$ (Boerhringer Mannheim) (1.3 μM) was prepared in a stirred cuvette. Coumarin peptide substrate (2 μL of a 1 mM solution in dimethyl sulfoxide) was added to the reaction mixture. The rate of hydrolysis was determined for about 100–200 seconds by measuring the fluorescence of the reaction at ex328 nanometers and em329 nanometers using a Hitachi F-2000 Fluorescence Spectrophotometer.

2 μL of a 10 mM inhibitor stock solution (in dimethyl sulfoxide) is added and the reduction in the rate of hydrolysis is determined. Additional 2 μL aliquots of the stock inhibitor solution is added until a 30% to 70% inhibition is observed. $K_i$ is calculated on the assumption of simple competitive inhibition and that the substrate concentration is much less than $K_m$. The results are shown in Table III.

TABLE III

INHIBITION DATA FOR 72 kD GELATINASE

| Compounds | $K_{i(app)}$ [nM] |
|---|---|
| 5-(N-t-butyloxycarbonyl-((O-benzyl)tyrosyl)-phenylglycylamino)-1,3,4-thiadiazole-2-thione | 0.51 |
| 5-(N-4-(4-t-butylphenylsulfonylamino)benzoyl)phenylalanyl-valylamino)-1,3,4-thiadiazole-2-thione | 0.68 |
| 5-(N-benzyloxycarbonyl-((p-benzyloxycarbonylamino)phenylalanyl)-valylamino)-1,3,4-thiadiazole-2-thione | 0.29 |
| 5-(N-benzyloxycarbonyl-phenylalanyl-methionyl-((O-benzyl)tyrosyl)-phenylglycylamino)-1,3,4-thiadiazole-2-thione | 0.2 |
| 5-(N-benzyloxycarbonyl-((O-benzyl)tyrosyl)-phenylglycylamino)-1,3,4-thiadiazole-2-thione | 0.145 |
| 5-(N-benzyloxycarbonyl-((O-benzyl)tyrosyl)-glycylamino)-1,3,4-thiadiazole-2-thione | 0.38 |
| 5-(N-(4-phenylbenzoyl)phenylalanyl-valylamino)-1,3,4-thiadiazole-2-thione | 0.80 |
| 5-(N-benzyloxycarbonyl-phenylalanyl-leucylamino)-1,3,4-thiadiazole-2-thione | 1.95 |
| 5-(N-benzyloxycarbonyl-glycyl-tyrosyl-((O-benzyl)tyrosyl)-phenylglycylamino)-1,3,4-thiadiazole-2-thione | 0.073 |
| 5-(N-benzyloxycarbonyl-(O-benzyl)tyrosyl-leucylamino)-1,3,4-thiadiazole-2-thione | 0.24 |
| 5-(N-benzyloxycarbonyl-(S-benzyl)cysteinyl-valylamino)-1,3,4-thiadiazole-2-thione | 1.1 |
| 5-(N-benzyloxycarbonyl-phenylalanyl-valylamino)-1,3,4-thiadiazole-2-thione | 4.6 |
| 5-(N-benzyloxycarbonyl-phenylalanyl-methionylamino)-1,3,4-thiadiazole-2-thione | 1.7 |
| 5-(N-benzyloxycarbonyl-((γ-N-2-phenylethyl)glutamyl)-phenylglycylamino)-1,3,4-thiadiazole-2-thione | 0.52 |
| 5-(N-benzyloxycarbonyl-phenylalanyl-tryptoyl-valylamino)-1,3,4-thiadiazole-2-thione | 0.71 |
| 5-(N-benzyloxycarbonyl-phenylalanyl-homophenylalanylamino)-1,3,4-thiadiazole-2-thione | 0.95 |

EXAMPLE 40

Assay of 92 KD Gelatinase Inhibition Activity

H-150 buffer, pH 7.4, was prepared by $CaCl_2H_2O$ (1.47 grams), NaCl (8.77 grams) and N-[2-hydroxyethyl]piperazine-N'-[2-ethanesulfonic acid](23.83 grams) to distilled and deionized water and then bring the final volume of the solution to 1 liter. A reaction mixture having a final volume of 500 μL was prepared with H-150 buffer, 200 μgrams of Pro-92KD gelatinase (Strongin et al., *J. Biol. Chem.*, 268:14033 (1993); Goldberg, et al., *J. Biol. Chem.*, 267:4583 (1992); Okada et al., *J. Biol. Chem.* 267:21712 (1992)), p-aminophenyl mercuric acetate (Sigma Chemical Co., St. Louis, Mo.) (1 mM) and Brij (dodexylpoly(oxyethyleneglycolether))(0.008% w/v). The reaction mixture wsa then incubated for 24 hours at 37° C.

The reaction mixture was applied to a NAP-5 column (G-25 SEPHADEX™, Pharmacia). Fractions containing 72KD gelatinase were identified using 12% polyacrylamide gel electrophoresis and concentrated to about 100–200 μliters by centrifigation (5000 g, 1 hour).

A solution containing H-150 buffer (2.0 mL), 92KD gelatinase (25 pM) and ethylphenolpoly(ethyleneglycolether)$_n$ (Boerhringer Mannheim) (4.0 μM) was prepared in a stirred cuvette. Coumarin peptide substrate (4 μL of a 5 mM solution in dimethyl sulfoxide) was added to the reaction mixture. The rate of hydrolysis was determined for about 100–200 seconds by measuring the fluorescence of the reaction at ex328 nanometers and em329 nanometers using a Hitachi F-2000 Fluorescence Spectrophotometer.

2 μL of a 10 mM inhibitor stock solution (in dimethyl sulfoxide) is added and the reduction in the rate of hydrolysis is determined. Additional 2 μL aliquots of the stock inhibitor solution is added until a 30% to 70% inhibition is observed. $K_i$ is calculated on the assumption of simple competitive inhibition and that the substrate concentration is much less than $K_m$. The results are shown in Table IV.

proceeding to make disks from the articulating surface of each plug. A 1 mm thick disk was sliced from individual plugs from the end that was the articulating surface of the joint. The plug was held steady in the sterile template (4 mm diameter×1.5 mm deep) using sterile forceps. A scalpel blade was used to carefully slice off the disk. Only the superficial articulating surface responded well in culture.

Individual disks obtained were transferred to a tissue culture flask containing about 100 mL fresh media. The flask containing the disks was placed in an incubator at 37° C. (with 5% $CO_2$, 95% air) and allowed to equilibrate overnight

TABLE IV

INHIBITION DATA FOR 92 kD GELATINASE

| Compound | $K_{i(app)}$ [nM] |
|---|---|
| 5-(N-t-butyloxycarbonyl-((O-benzyl)tyrosyl)-phenylglycylamino)-1,3,4-thiadiazole-2-thione | 0.245 |
| 5-(N-(4-(4-t-butylphenylsulfonylamino)benzoyl)phenylalanyl-valylamino)-1,3,4-thiadiazole-2-thione | 0.31 |
| 5-(N-benzyloxycarbonyl-((p-benzyloxycarbonylamino(phenylalanyl)-valylamino-1,3,4-thiadiazole-2-thione | 0.145 |
| 5-(N-benzyloxycarbonyl-phenylalanyl-alanylamino)-1,3,4-thiadiazole-2-thione | 3.6 |
| 5-(N-benzyloxycarbonyl-((O-benzyl)tyrosyl)phenylalanylamino)-1,3,4-thiadiazole-2-thione | 0.15 |
| 5-(N-benzyloxycarbonyl-phenylalanyl-tryptyl-valylamino)-1,3,4-thiadiazole-2-thione | 0.36 |
| 5-(N-4-phenylbenzoyl)phenylalanyl-valylamino)-1,3,4-thiadiazole-2-thione | 0.31 |
| 5-(N-benzyloxycarbonyl-phenylalanyl-leucylamino)-1,3,4-thiadiazole-2-thione | 2.3 |
| 5-(N-(9-fluorenylmethoxycarbonyl)-phenylalanylamino)-1,3,4-thiadiazole-2-thione | 0.23 |
| 5-(N-benzyloxycarbonyl-(O-benzyl)tyrosyl-leucylamino)-1,3,4-thiadiazole-2-thione | 0.29 |
| 5-(N-benzyloxycarbonyl-(S-benzyl)cysteinyl-valylamino)-1,3,4-thiadiazole-2-thione | 2.1 |
| 5-(N-benzyloxycarbonyl-phenylalanyl-valylamino)-1,3,4-thiadiazole-2-thione | 1.5 |
| 5-(N-benzyloxycarbonyl-phenylalanyl-methionylamino)1-3,4-thiadiazole-2-thione | 3.6 |
| 5-(N-benzyloxycarbonyl-((γ-N-2-phenylethyl)glutamyl)-phenylglycylamino)-1,3,4-thiadiazole-2-thione | 0.17 |
| 5-(N-benzyloxycarbonyl-prolyl-((O-benzyl)tyrosyl)-phenylglycylamino)-1,3,4-thiadiazole-2-thione | 0.76 |
| 5-(N-(9-fluorenylmethoxycarbonyl)-homophenylalanylamino)-1,3,4-thiadiazole-2-thione | 0.35 |

EXAMPLE 41

Inhibition of Cartilage Degradation in the Bovine Cartilage Explant Assay by Amino Acid Amide 5-Amino-1,3,4-Thiadiazole-2-Thiones A tissue culture assay was used to measure the ability of the compounds of the present invention to slow the degradation of the extracellular matrix by metalloproteinases. This assay measured the amount of $^{35}$S-glycosaminoglycan ($^{35}$S-GAG) released from labeled bovine cartilage explants.

Knee joints from a 1 to 3 week old calf were obtained immediately after sacrifice from the Abattoir and then transported on ice. The intact joints were washed well with tap water and soaked in 50% (v/v) Povidine iodine solution, obtained from Burre National, Inc., Baltimore, Md. All subsequent steps were performed in a laminar flow tissue culture hood using standard sterile technique. The joint was immobilized in a shank holder and the joint capsule was cut open to expose the articular cartilage. Cartilage explant plugs, approximately 15 mg wet weight, were removed from the flat articulating surfaces in the lower-most region of the knee joint using a sterile steel cork-borer and collected in a 250 mL roller bottle containing about 100 mL fresh Delbecco's minimum essential medium (DMEM), obtained from Gibco BRC, Life Technologies, Gaithersburg, Md., containing 4.5 g/l (D)-glucose and (L)-glutamine, without sodium pyruvate. The fresh media also contained enough Hepes buffer and sodium bicarbonate such that the pH was about 7.4. The media was then further supplemented just before use with 100 units Penicillin, 100 μg Streptomycin, and 50 μg (L)-ascorbic acid per mL of medium.

Once collected, the explant plugs were washed four times with 50 mL fresh DMEM. The plugs were then placed in the incubator for a minimum of 1 hour to equilibrate, before and at least one additional day before labeling. When ready to label, the old media was replaced with 50 mL fresh media containing about 500 μCi $^{35}$S-Sodium Sulfate. The plugs were labeled in bulk for about 48 hours. The next morning, the "hot" media was removed and replaced with fresh "cold" media. The disks were again allowed to equilibrate overnight before being used for actual experiments.

The media in which the disks were stored was changed immediately prior to performing the assay. The disks were then returned to the incubator until the test media and the two control media had been prepared. The test media consisted of the desired concentration of a compound being tested for its ability to inhibit extracellular matrix degradation and concomitant recombinant human Interleukin rhIL-1α (5 ng/mL) in fresh DMEM solution. The control media were identical to the test media, except that the first control media lacked rhIL-1α and the second control media lacked the test compound. 250 μL of each of the test and control media were transferred to separate 96-well TC plates. Flamed forceps were used to transfer a disk from the incubator to each 96-well TC plates that had been filled with either the test media or one of the two control media.

The TC plates were then placed in the incubator and cultured for 3–4 days (initial incubation with rhIL-1α alpha takes at least 3 days to stimulate endogenous metalloproteinases). A 50 μL aliquot of media from each TC plate was saved and counted. The rest of the media was removed with a suction device.

The cartilage disks from each TC plate were also saved for counting. The disks were removed with forceps and placed in microcentrifuge tubes and then dissolved in 250 μL of full strength formic acid. The tubes were capped and placed at 65°–70° C. in a block-heater for 4–6 hours. A 50 μL aliquot was then counted.

The percent $^{35}$S-GAG release is calculated as follows:

% $^{35}$S-GAG release={(cpm$_{medium}$)/(cpm$_{medium}$+cpm$_{explant}$)}×100%

The percent inhibition of extracellular matrix damage in cartilage explant was calculated as follows:

% Inhibition = $\frac{(A-B)-(C-B)}{(A-B)} \times 100$, wherein
A=% GAG release induced by rhIL-1α;
B=% GAG release in the absence of rhIL-1α; and
C=% GAG release in the presence of rhIL-1α plus the compound being tested.

The percent inhibition of amino acid amides of 5-amino-1,3,4-thiadiazole-2-thione and the concentrations at which they were tested are given in Table V below.

TABLE V

THE INHIBITION OF PLASMINOGEN/IL-1 STIMULATED CARTILAGE DEGRADATION BY 5-AMINO-1,3,4-THIADIAZOLE-5-THIONE DERIVATIVES

| Compounds | % inhibition (concentration [μM]) |
|---|---|
| 5-(N-benzyloxycarbonyl-phenylalanyl-leucylamino)-1,3,4-thiadiazole-2-thione | 33% (50) |
| 5-(N-(9-fluorenylmethoxycarbonyl)valylamino)-1,3,4-thiadiazole-2-thione | 42% (20) |
| 5-(N-benzyloxycarbonyl-phenylalanyl-valylamino)-1,3,4-thiadiazole-2-thione | 40% (10) |
| 5-(N-benzyloxycarbonyl-tryptolyl-phenylalanylamino)-1,3,4-thiadiazole-2-thione | 35% (50) |
| 5-(N-benzyloxycarbonyl-((O-benzyl)tyrosyl)-valylamino)-1,3,4-thiadiazole-2-thione | 59% (50) |
| 5-(N-benzyloxycarbonyl-((O-benzyl)glutamoyl)-valylamino-1,3,4-thiadiazole-2-thione | 33% (25) |
| 5-(N-benzyloxycarbonyl-D-homophenylalanylamino)-1,3,4-thiadiazole-2-thione | 22% (25) |
| 5-(N-(4-phenyl)phenylacetyl-phenylalanyl-valylamino)-1,3,4-thiadiazole-2-thione | 37% (25) |
| 5-(N-benzyloxycarbonyl-((NH-trityl)glutamyl)-valylamino)-1,3,4-thiadiazole-2-thione | 56% (25) |
| 5-(N-(4-phenyl)phenylacetyl-valylamino)-1,3,4-thiadiazole-2-thione | 47% (25) |
| 5-(N-benzyloxycarbonyl-((O-benzyl)tyrosyl)-phenylglycylamino)-1,3,4-thiadiazole-2-thione | 20% (25) |
| 5-(N-(9-fluorenylmethoxycarbonyl-homophenylalanylamino-1,3,4-thiadiazole-2-thione | 65% (50) |

Equivalents

Those skilled in the art will know, or be able to ascertain using no more than routine experimentation, many equivalents to the specific embodiments of the invention described herein. These and all other equivalents are intended to be encompassed by the following claims.

We claim:

1. A compound represented by the following structural formula:

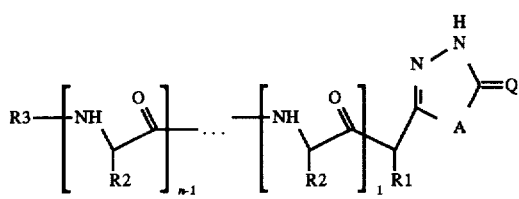

wherein:
Q and A are each independently selected from the group consisting of sulfur and oxygen and at least one of Q and A is sulfur;
n is a positive integer which results in a matrix metalloproteinase inhibitor;
R1 is selected from the group consisting of —H, lower alkyl and acyl;
each R2 is independently selected from the group consisting of $C_1$–$C_{10}$ straight or branched alkyl, $C_1$–$C_{10}$ straight or branched substituted alkyl, $C_3$–$C_8$ cyclic alkyl, substituted $C_3$–$C_8$ cyclic alkyl, $C_1$–$C_{10}$ straight or branched alkenyl, $C_1$–$C_{10}$ straight or branched substituted alkenyl, $C_1$–$C_{10}$ straight or branched alkynyl, $C_1$–$C_{10}$ straight or branched substituted alkenyl, aryl, substituted aryl, heteroaryl, substituted heteroaryl;

R3 is selected from the group consisting of an amine protecting group X—CO—, X—CS—, X—S$_2$—, X—O—CO— and X—O—CS—;

X is selected from the group consisting of $C_1$–$C_{10}$ alkyl, $C_1$–$C_{10}$ substituted alkyl, aryl, substituted aryl, heteroaryl and substituted heteroaryl; or
a physiologically active salt thereof.

2. The compound of claim 1, wherein:
n is an integer from 1–10;
R1 is —H; and
R3 is selected from the group consisting of X—CO—, X—CS—, X—SO$_2$—, X—O—CO— and X—O—CS—.

3. The compound of claim 2, wherein;
A and Q are each sulfur; and
each R2 is selected from the group consisting of a side chain of a naturally occurring amino acid, (substituted phenyl)-CH$_2$—, napthyl-CH$_2$—, (O-substituted) tyrosyl, cycloalkyl, (O-substituted)glutamoyl, (S-substituted)cysteinyl, (O-substituted) seryl, (N-substituted)glutamyl, (N,N-disubstituted)glutamyl, (N-ε-substituted)lysyl, aryl and substituted aryl.

4. The compound of claim 3, wherein:
n is an integer from 1–4; and
R3 is benzyloxycarbonyl, 9-fluorenylmethoxycarbonyl, t-butoxycarbonyl, (4-phenyl)phenylacetyl, 8-quinolinesulfonyl, 2-methylthionicotyl, xanthene-9-carbonyl, hydrocinamoyl, phenylbenzoyl, nonanoyl, (4-benzyloxy)benzoyl, acetyl and (4-(4-t-butylphenylsulfonamino)benzoyl.

5. The compound of claim 4, wherein:
R2 is selected from the group consisting of phenyl, cylcohexyl and the side chain of (O-benzyl)tyrosine, (O-methylene-2-naphtyl)tyrosyl, (N-trityl)glutamyl, (N,N-dibenzyl)glutamyl, (N-2-phenylethyl)glutamyl, phenylalanine, valine and tryptophan; and
R3 is selected from the group consisting of 4-phenylbenzoyl, nonanoyl, benzyloxybenzoyl and (4-(4-t-butylphenylsulfonamino)benzoyl.

6. The compound of claim 5, wherein the compound is 5-(N-(4-(4-t-butylphenylsulfonamino)benzoyl)- phenylalanyl-valylamino)-1,3,4-thiadiazole-2-thione, 5-(N-benzyloxycarbonyl-(O-benzyl)tyrolsyl-phenylglycylamino)-1,3,4-thiadiazole-2-thione and N-(N-benzyloxycabonyl)-((N,N-dibenzyl)glutamyl)-phenylglycyamino)-1,3,4-thiadiazole-2-thione.

7. A method of inhibiting a matrix metalloproteinase, comprising contacting the matrix metalloproteinase with an inhibitory amount of a compound represented by the following structural formula:

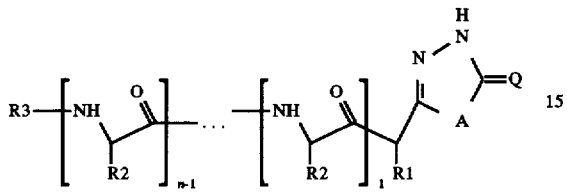

wherein:

Q and A are each independently selected from the group consisting of sulfur and oxygen and at least one of Q and A is sulfur;

n is a positive integer which results in a matrix metalloproteinase inhibitor;

R1 is selected from the group consisting of —H, lower alkyl and acyl;

each R2 is independently selected from the group consisting of $C_1$–$C_{10}$ straight or branched alkyl, $C_1$–$C_{10}$ straight or branched substituted alkyl, $C_3$–$C_8$ cyclic alkyl, substituted $C_3$–$C_8$ cyclic alkyl, $C_1$–$C_{10}$ straight or branched alkenyl, $C_1$–$C_{10}$ straight or branched substituted alkenyl, $C_1$–$C_{10}$ straight or branched alkynyl, $C_1$–$C_{10}$ straight or branched substituted alkenyl, aryl, substituted aryl, heteroaryl, substituted heteroaryl;

R3 is selected from the group consisting of an amine protecting group X—CO—, X—CS—, X—SO$_2$—, X—O—CO— and X—O—CS—;

X is selected from the group consisting of $C_1$–$C_{10}$ alkyl, $C_1$–$C_{10}$ substituted alkyl, aryl, substituted aryl, heteroaryl and substituted heteroaryl; or a physiologically active salt thereof.

8. The method of claim 7, wherein:

Q and A are each sulfur;

n is an integer from 1–10;

R1 is —H;

R3 is selected from the group consisting of X—CO—, X—CS—, X—SO$_2$—, X—O—CO— and X—O—CS—.

9. The method of claim 8, wherein:

n is an integer from 1–4;

each R2 is selected from the group consisting of a side chain of a naturally occurring amino acid, (substituted phenyl)-CH$_2$—, napthyl-CH$_2$—, (O-substituted) tyrosyl, cycloalkyl, (O-substituted)glutamoyl, (S-substituted)cysteinyl, (O-substituted) seryl, (N-substituted)glutamyl, (N,N-disubstituted) glutamyl, (N-ε-substituted)lysyl, aryl and substituted aryl; and R3 is benzyloxycarbonyl, 9-fluorenylmethoxycarbonyl, t-butoxycarbonyl, (4-phenyl)phenylacetyl, 8-quinolinesulfonyl, 2-methylthionicotyl, xanthene-9-carbonyl, hydrocinamoyl, phenylbenzoyl, nonanoyl, (4-benzyloxy)benzoyl, acetyl and (4-(4-t-butylphenylsulfonamino)benzoyl.

10. The method of claim 9, wherein the matrix metalloproteinase is selected from the group consisting of interstitial collagenase, stromelysin, gelatinases and human neutrophil collagenase.

11. A method for treating an individual with a disease, wherein said disease is ameliorated by inhibiting at least one matrix metalloproteinase enzyme, comprising administering a therapeutically effective amount of a compound represented by the following structural formula:

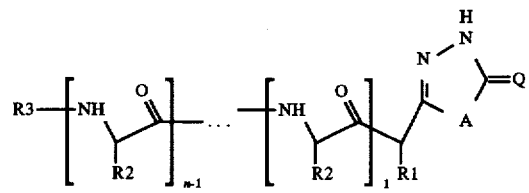

wherein:

Q and A are each independently selected from the group consisting of sulfur and oxygen and at least one of Q and A is sulfur;

n is a positive integer which results in a matrix metalloproteinase inhibitor;

R1 is selected from the group consisting of —H, lower alkyl and acyl;

each R2 is independently selected from the group consisting of $C_1$–$C_{10}$ straight or branched alkyl, $C_1$–$C_{10}$ straight or branched substituted alkyl, $C_3$–$C_8$ cyclic alkyl, substituted $C_3$–$C_8$ cyclic alkyl, $C_1$–$C_{10}$ straight or branched alkenyl, $C_1$–$C_{10}$ straight or branched substituted alkenyl, straight or branched alkynyl, $C_1$–$C_{10}$ straight or branched substituted alkenyl, aryl, substituted aryl, heteroaryl, substituted heteroaryl;

R3 is selected from the group consisting of an amine protecting group X—CO—, X—CS—, X—SO$_2$—, X—O—CO— and X—O—CS—;

X is selected from the group consisting of $C_1$–$C_{10}$ alkyl, $C_1$–$C_{10}$ substituted alkyl, aryl, substituted aryl, heteroaryl and substituted heteroaryl; or a physiologically active salt thereof.

12. The method of claim 11, wherein the disease is osteoarthritis.

13. The method of claim 11, wherein the disease is rheumatoid arthritis.

14. The method of claim 11, wherein the disease is cancer.

15. The method of claim 11, wherein the inhibition of at least one matrix metlloproteinase enzyme results in a decrease in inflammation caused by the disease.

16. The method of claim 12, wherein:

n is an integer from 1–10;

R1 is —H;

R3 is selected from the group consisting of X—CO—, X—CS—, X—SO$_2$—, X—O—CO— and X—O—CS—.

17. The method of claim 16, wherein:

n is an integer from 1–4;

each R2 is selected from the group consisting of a side chain of a naturally occurring amino acid, (substituted phenyl)-CH$_2$—, napthyl-CH$_2$—, (O-substituted)

tyrosyl, cycloalkyl, (O-substituted)glutamoyl, (S-substituted)cysteinyl, (O-substituted) seryl, (N-substituted)glutamyl, (N,N-disubstituted)glutamyl, (N-ε-substituted) lysyl, aryl and substituted aryl; and R3 is benzyloxycarbonyl, 9-fluoerenylmethoxycarbonyl, t-butoxycarbonyl, (4-phenyl)phenylacetyl, 8-quinolinesulfonyl, 2-methylthionicotyl, xanthene-9-carbonyl, hydrocinamoyl, phenylbenzoyl, nonanoyl, (4-benzyloxy)benzoyl, acetyl and (4-(4-t-butylphenylsulfonamino)benzoyl.

* * * * *